United States Patent
Strahan et al.

(10) Patent No.: US 11,033,752 B2
(45) Date of Patent: Jun. 15, 2021

(54) PHOTOBIOMODULATION THERAPY SYSTEMS AND METHODS

(71) Applicant: Joovv, Inc., San Clemente, CA (US)

(72) Inventors: Justin Strahan, San Clemente, CA (US); Scott Nelson, San Clemente, CA (US)

(73) Assignee: Joovv, Inc., San Clemente, CA (US)

(*) Notice: Subject to any disclaimer, the term of this patent is extended or adjusted under 35 U.S.C. 154(b) by 0 days.

(21) Appl. No.: 16/167,385

(22) Filed: Oct. 22, 2018

(65) Prior Publication Data
US 2020/0121944 A1    Apr. 23, 2020

(51) Int. Cl.
*A61N 5/06*    (2006.01)
*A61N 5/067*   (2006.01)

(52) U.S. Cl.
CPC .... *A61N 5/0616* (2013.01); *A61N 2005/0633* (2013.01); *A61N 2005/0645* (2013.01); *A61N 2005/0651* (2013.01); *A61N 2005/0652* (2013.01); *A61N 2005/0659* (2013.01); *A61N 2005/0662* (2013.01); *A61N 2005/0663* (2013.01)

(58) Field of Classification Search
None
See application file for complete search history.

(56) References Cited

U.S. PATENT DOCUMENTS

| 4,844,069 A | 7/1989 | Mori |
| 5,645,578 A | 7/1997 | Daffer |
| 5,733,032 A | 3/1998 | Bolta |
| 5,800,478 A * | 9/1998 | Chen ................ A61B 17/00234 607/88 |

(Continued)

FOREIGN PATENT DOCUMENTS

| KR | 101244434 B1 | 3/2013 |
| WO | 2018152278 | 8/2018 |

(Continued)

OTHER PUBLICATIONS

Kind LED Grow Lights, "Kind LED Grow Lights K5 Series Instructions"—Downloaded on Oct. 1, 2018 from https://www.kindledgrowlights.com/pages/k5-setup.

(Continued)

*Primary Examiner* — Carl H Layno
*Assistant Examiner* — Manolis Pahakis
(74) *Attorney, Agent, or Firm* — Wesley E. Schwie, Esq.; Gallium Law, LLC

(57) ABSTRACT

Photobiomodulation therapy systems provide a highly effective way to treat many common ailments to the human body. Many embodiments described herein enable two or more light therapy devices to be coupled together in various ways. In some embodiments, the light therapy system includes a first light device and a second light device arranged and configured to be mechanically and/or electrically coupled to the first light device. Each of the light devices may include a housing and a plurality of lights arranged and configured to emit at least one of red light and near infrared light. The first light device and the second light device can be coupled in a side-by-side orientation or a top-to-bottom orientation. The light therapy system can also be coupled to a mobile stand or a door stand.

20 Claims, 23 Drawing Sheets

(56) References Cited

U.S. PATENT DOCUMENTS

| | | | |
|---|---|---|---|
| 6,626,932 B2 | 9/2003 | Whitehurst | |
| 6,955,684 B2* | 10/2005 | Savage, Jr. | A61N 5/0618 607/88 |
| 7,033,381 B1* | 4/2006 | Larsen | A61N 5/0616 607/88 |
| 8,066,403 B2* | 11/2011 | Sanfilippo | F21S 2/005 362/219 |
| 8,337,538 B1 | 12/2012 | Ford | |
| 8,481,982 B2 | 7/2013 | Johnson | |
| 9,227,082 B2 | 1/2016 | McDaniel | |
| 9,311,847 B2* | 4/2016 | Hall | G09G 3/3208 |
| 9,353,924 B2* | 5/2016 | Scarlata | F21S 9/00 |
| 9,416,551 B2* | 8/2016 | Hall | G09F 21/04 |
| 9,440,041 B1 | 9/2016 | Lacayo | |
| 9,852,666 B2* | 12/2017 | Ward | G09F 9/3026 |
| 9,884,204 B1 | 2/2018 | Dolleris | |
| 9,943,042 B2* | 4/2018 | Thosteson | H05B 37/0272 |
| 10,440,794 B2 | 10/2019 | Alexander | |
| 2003/0009205 A1* | 1/2003 | Biel | A61N 5/0601 607/88 |
| 2003/0188378 A1 | 10/2003 | Brunelle | |
| 2004/0008523 A1 | 1/2004 | Butler | |
| 2004/0014199 A1* | 1/2004 | Streeter | A61N 5/0613 435/284.1 |
| 2004/0068305 A1 | 4/2004 | Bansal | |
| 2004/0162596 A1 | 8/2004 | Altshuler | |
| 2004/0193234 A1* | 9/2004 | Butler | A61N 5/0616 607/88 |
| 2005/0075703 A1* | 4/2005 | Larsen | A61N 5/062 607/88 |
| 2005/0085875 A1* | 4/2005 | Van Zuylen | A61N 5/0616 607/88 |
| 2005/0237739 A1* | 10/2005 | Lee | A61N 5/0613 362/241 |
| 2006/0007059 A1* | 1/2006 | Bell | A41D 27/085 345/55 |
| 2006/0020308 A1* | 1/2006 | Muldner | A61N 5/0616 607/88 |
| 2006/0217789 A1 | 9/2006 | Perez | |
| 2006/0229689 A1 | 10/2006 | Ferguson | |
| 2007/0068055 A1* | 3/2007 | Segan | G09F 9/33 40/544 |
| 2007/0129777 A1 | 6/2007 | Bolta | |
| 2007/0217199 A1 | 9/2007 | Adam | |
| 2007/0276455 A1* | 11/2007 | Fiset | A61C 19/066 607/91 |
| 2008/0046044 A1* | 2/2008 | Jahnigen | A61N 5/06 607/100 |
| 2008/0091250 A1* | 4/2008 | Powell | A61M 21/00 607/90 |
| 2008/0114418 A1* | 5/2008 | Myeong | A61N 5/0613 607/89 |
| 2008/0119831 A1* | 5/2008 | Myeong | A61N 5/0613 606/13 |
| 2008/0141572 A1* | 6/2008 | Tomich | G09F 9/30 40/605 |
| 2008/0269849 A1* | 10/2008 | Lewis | A61N 5/0613 607/91 |
| 2009/0288340 A1 | 11/2009 | Hess | |
| 2009/0318908 A1* | 12/2009 | Van Pieterson | A61B 5/0059 606/9 |
| 2010/0045175 A1* | 2/2010 | Mathai | H01L 27/3209 313/504 |
| 2010/0045189 A1* | 2/2010 | Storch | H01L 51/50 315/149 |
| 2010/0076529 A1* | 3/2010 | Tucker | A61N 5/0616 607/90 |
| 2010/0277105 A1* | 11/2010 | Oyama | H05B 47/11 315/312 |
| 2010/0309659 A1 | 12/2010 | Jenny | |
| 2011/0054573 A1* | 3/2011 | Mitchell | A61N 5/0618 607/90 |
| 2012/0019490 A1* | 1/2012 | Huang | G09G 3/32 345/205 |
| 2012/0030873 A1* | 2/2012 | Turtzo | A47C 21/003 5/421 |
| 2012/0104977 A1 | 5/2012 | McKenzie | |
| 2012/0243227 A1* | 9/2012 | Shimizu | F21S 8/04 362/249.01 |
| 2012/0296260 A1 | 11/2012 | Vizethum | |
| 2013/0172963 A1 | 7/2013 | Moffat | |
| 2013/0190842 A1* | 7/2013 | Hacco | A61N 5/06 607/89 |
| 2013/0229802 A1* | 9/2013 | Fukushima | F21V 19/003 362/235 |
| 2013/0301264 A1* | 11/2013 | Van Gompel | F21S 2/005 362/236 |
| 2013/0304019 A1 | 11/2013 | Cooper | |
| 2014/0081357 A1* | 3/2014 | Legerton | F21S 8/04 607/88 |
| 2014/0190537 A1 | 7/2014 | Benda | |
| 2014/0226329 A1* | 8/2014 | Oraw | H01L 25/0753 362/235 |
| 2015/0202455 A1* | 7/2015 | Williams | A61N 5/06 607/90 |
| 2015/0267907 A1* | 9/2015 | Thompson | F21V 23/06 362/249.06 |
| 2015/0297914 A1* | 10/2015 | Hamid | A61N 5/0617 607/89 |
| 2015/0307332 A1 | 10/2015 | Huang | |
| 2016/0016001 A1 | 1/2016 | Loupis | |
| 2016/0076708 A1* | 3/2016 | Shirilla | F21S 2/005 362/235 |
| 2016/0158574 A1* | 6/2016 | Eckhouse | A61H 7/008 607/89 |
| 2016/0175610 A1 | 6/2016 | Livingston | |
| 2016/0367833 A1* | 12/2016 | Salinas | A61F 7/007 |
| 2017/0028216 A1 | 2/2017 | Medendorp | |
| 2017/0080246 A1 | 3/2017 | Knight | |
| 2017/0118838 A1* | 4/2017 | Williams | H05K 3/4691 |
| 2017/0131693 A1 | 5/2017 | Shurtleff | |
| 2018/0043178 A1* | 2/2018 | Iguchi | A61N 5/0616 |
| 2018/0056087 A1 | 3/2018 | Ribeiro | |
| 2018/0111001 A1* | 4/2018 | Segel | A61N 5/0616 |
| 2018/0236259 A1* | 8/2018 | Nelson | A61N 5/0616 |
| 2018/0345034 A1* | 12/2018 | Butzloff | A61N 5/0613 |
| 2019/0167519 A1 | 6/2019 | Kaps | |

FOREIGN PATENT DOCUMENTS

| | | |
|---|---|---|
| WO | 2020086494 | 4/2020 |
| WO | 2020131235 | 6/2020 |

OTHER PUBLICATIONS

Mouser Electronics, "Enclosures and Racks"—Downloaded on Oct. 4, 2018 from http://www.mouser.com/catalog/catalogusd/648/dload/pdf/ENCLOSECTION.pdf; prior art publication at least as of 2015.

Kind LED Grow Lights, "Kind LED Grow Lights—Voted Best LED Grow Lights of 2014!"—Downloaded on Oct. 2, 2018 from https://www.youtube.com/watch?v=NQDWBXIMxrk; prior part publication at least as of May 26, 2017.

Wrethaoffgrid, "Ohuhu Pair of 1/8" Grow Light Rope Hanger Review"—Downloaded on Oct. 5, 2018 from https://www.youtube.com/watch?v=gYCsNQ9LELM; prior art publication at least as of Sep. 29, 2016.

OXO, "OXO Over the Door Hooks & Racks"—Downloaded on Oct. 5, 2018 from https://www.youtube.com/watch?v=1WziS-a7LMl; prior part publication at least as of Feb. 11, 2014.

Woodworkers Store, "Swivel Mirror Screw"—Downloaded on Oct. 4, 2018 from http://go.rockler.com/tech/Swivel-Mirror-Screws-Instructions.pdf; prior art publication at least as of 1990.

Kind LED Grow Lights, "K5 Series XL1000 Indoor LED Grow Light"—Downloaded on Oct. 4, 2018 form https://www.kindledgrowlights.com/products/k5-xl1000.

(56) References Cited

OTHER PUBLICATIONS

Swedish LED Grow Lights, "300W Full Spectrum Led Grow Lights 85-265V 5730SMD USA/DE/AU/CA Stock Hanging Kit for Plants Veg Hydroponics Grow Led"—Downloaded on Jun. 5, 2017 from http://swedishledgrowlights.com/product/300w-full-spectrum-led-grow-lights-85-265v-5730smd-usa-de-au-ca-stock-hanging-kit-for-plants-veg-hydroponics-grow-led/.

PCT International Search Report and Written Opinion in International Application No. PCT/US2018/018288, dated Oct. 29, 2018, 11 pages.

PCT International Preliminary Report on Patentability in International Application No. PCT/US2018/018288, dated Aug. 20, 2019, 9 pages.

PCT International Search Report and Written Opinion in International Application No. PCT/US2019/059845, dated Dec. 11, 2019, 7 pages.

PCT International Search Report and Written Opinion in International Application No. PCT/US2019/057292, dated Jan. 7, 2020, 8 pages.

PCT International Search Report and Written Opinion in International Application No. PCT/US2020/038187, dated Aug. 19, 2020, 8 pages.

\* cited by examiner

PHOTOBIOMODULATION THERAPY SYSTEMS AND METHODS

CROSS-REFERENCE TO RELATED APPLICATIONS

The entire contents of the following application are incorporated by reference herein: U.S. patent application Ser. No. 15/616,028; filed Jun. 7, 2017; and entitled THERAPEUTIC LIGHT SOURCE AND HANGING APPARATUS.

BACKGROUND

Field

Various embodiments disclosed herein relate to photobiomodulation therapy systems and methods.

Background

Photobiomodulation therapy (or light therapy) is a therapeutic technique that uses low-level wavelengths of light to improve health and treat a variety of health conditions, including skin issues, such as wrinkles, scars, and persistent wounds, among many other conditions. Similar to how plants use sunlight to heal and grow, humans and animals are able to harness these wavelengths of light and turn them into cellular energy. This treatment stimulates the body's natural healing processes.

Currently, there are a number of photobiomodulation therapy devices available on the market. However, many of these devices are too small and require multiple sessions to treat large areas. As a result, there is a need for a photobiomodulation therapy system that can treat several areas in fewer treatments.

SUMMARY

The disclosure includes a variety of embodiments whereby two or more light devices are electrically and/or mechanically coupled together to form a modular photobiomodulation therapy system. The term "photobiomodulation" shall be used interchangeably with the term "light". For the purposes of this disclosure, "photobiomodulation" and "light" shall include wavelengths of light in the red, blue, green, and near infrared spectrums.

In some embodiments, the photobiomodulation therapy system includes a first light device and a second light device arranged and configured to be coupled to the first light device. The first light device may include a first housing and a first plurality of lights arranged and configured to emit at least one of red light, blue light, green light, and/or near infrared light. Additionally, the second light device may include a second housing and a second plurality of lights arranged and configured to emit at least one of red light, blue light, green light, and/or near infrared light. In some embodiments, the first light device is arranged and configured to be electrically coupled to the second light device.

In many embodiments, the first light device comprises a first power management system electrically coupled to the first plurality of lights, and the second light device comprises a second power management system electrically coupled to the second plurality of lights. Embodiments may thereby include a first power cord arranged and configured to be electrically coupled to the first power management system and a first power outlet. Additionally, embodiments may include a second power cord arranged and configured to be electrically coupled to the first power management system and the second power management system. This may allow the first light device and the second light device to be electrically paired together in series.

The photobiomodulation therapy system can be expanded by adding a third light device arranged and configured to be coupled to at least one of the first light device and the second light device, and a fourth light device arranged and configured to be coupled to at least one of the first light device, second light device, and third light device. The third light device may include a third housing, a third plurality of lights arranged and configured to emit at least one of red light, blue light, green light, and/or near infrared light, and a third power management system electrically coupled to the third plurality of lights. Accordingly, the fourth light device may include a fourth housing, a fourth plurality of lights arranged and configured to emit at least one of red light, blue light, green light, and/or near infrared light, and a fourth power management system electrically coupled to the fourth plurality of lights. Embodiments may thereby include a third power cord arranged and configured to be electrically coupled to the third power management system and a second power outlet. Additionally, embodiments may include a fourth power cord arranged and configured to be electrically coupled to the third power management system and the fourth power management system. This may allow the third light device and the fourth light device to be electrically coupled in series, and these together are in parallel with the first light device and the second light device.

Embodiments may also include a third power cord that can be arranged and configured to be electrically coupled to the second power management system and a third power management system. Additionally, embodiments may include a fourth power cord that may also be arranged and configured to be electrically coupled to the third power management system and the fourth power management system. This may allow the first light device, second light device, third light device, and fourth light device to all be electrically coupled in series.

The photobiomodulation therapy system can further be expanded to include a fifth light device arranged and configured to be coupled to at least one of the first light device, second light device, third light device, and fourth light device, and a sixth light device arranged and configured to be coupled to at least one of the first light device, second light device, third light device, fourth light device, and fifth light device. The fifth light device may include a fifth housing, a fifth plurality of lights arranged and configured to emit at least one of red light, blue light, green light, and/or near infrared light, and a fifth power management system electrically coupled to the fifth plurality of lights. Likewise, the sixth light device may include a sixth housing, a sixth plurality of lights arranged and configured to emit at least one of red light, blue light, green light, and/or near infrared light, and a sixth power management system electrically coupled to the sixth plurality of lights. Such embodiments may thereby include a fourth power cord electrically coupled to the second power outlet. Additionally, embodiments may include a fifth power cord arranged and configured to be electrically coupled to the fourth power management system and the fifth power management system, and a sixth power cord arranged and configured to be electrically coupled to the fifth power management system and the sixth power management system. This may allow the fourth light device, fifth light device, and sixth light device to be electrically coupled in series, and paired together in parallel with the first, second, and third light devices.

Alternatively, embodiments may be configured whereby all of the light devices are coupled together in series. In this regard, embodiments may thereby include the fourth power cord arranged and configured to be electrically coupled to the third power management system and the fourth power management system. Accordingly, embodiments may include a fifth power cord arranged and configured to be electrically coupled to the fourth power management system and a fifth power management system, and a sixth power cord arranged and configured to be electrically coupled to the fifth power management system and the sixth power management system. As previously stated, this may allow the first light device, second light device, third light device, fourth light device, fifth light device, and sixth light device to all be electrically coupled in series.

In addition to electrical coupling, two or more light devices may be mechanically coupled together to form a variety of sizes and configurations. In some embodiments, the system includes a first aperture located on a bottom side of the first housing, and a second aperture located on the bottom side of the first housing. Additionally, embodiments may include a first attachment member extending from a top surface of the second housing. The first attachment member may be arranged and configured to be detachably coupled to the first aperture to thereby couple the first housing to the second housing. Accordingly, embodiments may include a second attachment member extending from the top surface of the second housing. The second attachment member may be arranged and configured to be detachably coupled to the second aperture to thereby couple the first housing to the second housing. Mechanically coupling the first light device and the second light device in this way achieves a top-to-bottom orientation.

Alternatively, some embodiments may be mechanically coupled in a side-by-side orientation. In some embodiments, the system includes a first bracket arranged and configured to be detachably coupled to a back side of the first housing and a back side of the second housing to thereby detachably couple the first housing to the second housing. Additionally, some embodiments include a second bracket arranged and configured to be detachably coupled to the back side of the first housing and the back side of the second housing to detachably couple the first housing to the second housing.

In some embodiments, the system includes a door stand to thereby mount the light therapy system to a door. In this regard, some embodiments include a first attachment member extending from a top surface of the first housing. The first attachment member may be arranged and configured to be detachably coupled to a first door stand. Additionally, some embodiments include a second attachment member extending from the top surface of the first housing. The second attachment member may be arranged and configured to be detachably coupled to the first door stand. Accordingly, some embodiments include a third attachment member extending from a top surface of the second housing. The third attachment member may be arranged and configured to be detachably coupled to a second door stand. Additionally, some embodiments include a fourth attachment member extending from the top surface of the second housing. Likewise, the fourth attachment member may be arranged and configured to be detachably coupled to the second door stand.

From a mechanical coupling perspective, the light therapy system can be expanded by adding a third light device arranged and configured to be detachably coupled to at least one of the first light device and the second light device, and a fourth light device arranged and configured to be detachably coupled to at least one of the first light device, second light device, and third light device. The third light device may include a third housing and a third plurality of lights arranged and configured to emit at least one of red light, blue light, green light, and/or near infrared light. Accordingly, the fourth light device may include a fourth housing and a fourth plurality of lights arranged and configured to emit at least one of red light, blue light, green light, and/or near infrared light. Some embodiments include a third bracket arranged and configured to be detachably coupled to a back side of the third housing and a back side of the fourth housing to thereby detachably couple the third housing to the fourth housing. Additionally, some embodiments include a fourth bracket arranged and configured to be detachably coupled to the back side of the third housing and the back side of the fourth housing to thereby detachably couple the third housing to the fourth housing.

Even still, in some embodiments, the system includes a first aperture and a second aperture both located on a bottom side of the first housing, and a third aperture and a fourth aperture both located on a bottom side of the second housing. Some embodiments may thereby include a fifth attachment member extending from a top surface of the third housing. The fifth attachment member may be arranged and configured to be detachably coupled to the first aperture. Accordingly, some embodiments include a sixth attachment member extending from the top surface of the third housing. The sixth attachment member may be arranged and configured to be detachably coupled to the second aperture. Some embodiments may also include a seventh attachment member extending from a top surface of the fourth housing. The seventh attachment member may be arranged and configured to be detachably coupled to the third aperture. Even still, some embodiments may include an eighth attachment member extending from the top surface of the fourth housing. The eighth attachment member may be arranged and configured to be detachably coupled to the fourth aperture.

Some system embodiments disclosed herein include a mobile stand. In this regard, the first housing and the second housing may include a top side, a bottom side, a front side, and a back side. The system may further include a third light device arranged and configured to be detachably coupled to at least one of the first light device and the second light device, and a fourth light device arranged and configured to be detachably coupled to at least one of the first light device, the second light device, and the third light device. In some embodiments, the third light device includes a third housing and a third plurality of lights arranged and configured to emit at least one of red light, blue light, green light, and/or near infrared light. Accordingly, in some embodiments, the fourth light device includes a fourth housing and a fourth plurality of lights arranged and configured to emit at least one of red light, blue light, green light, and/or near infrared light. Additionally, some embodiments include a first bracket arranged and configured to be detachably coupled to a back side of the first housing and a back side of the second housing to thereby detachably couple the first housing to the second housing. Similarly, some embodiments include a second bracket arranged and configured to be detachably coupled to a back side of the third housing and a back side of the fourth housing to thereby detachably couple the third housing to the fourth housing. Some embodiments include a quad bracket arranged and configured to be detachably coupled to the back side of the first housing, the back side of the second housing, the back side of the third housing, and the back side of the fourth housing to thereby detachably couple the first housing, second housing, third housing, and fourth housing together. The quad bracket may be arranged and configured to be detachably coupled to a mobile stand.

In some embodiments, the first housing and the second housing may include a top side, a bottom side, a front side, and a back side. The system may further include a third light device arranged and configured to be detachably coupled to at least one of the first light device and the second light device, a fourth light device arranged and configured to be detachably coupled to at least one of the first light device, the second light device, and the third light device, a fifth light device arranged and configured to be detachably coupled to at least one of the first light device, the second light device, the third light device, and the fourth light device, and a sixth light device arranged and configured to be detachably coupled to at least one of the first light device, the second light device, the third light device, the fourth light device, and the fifth light device. In some embodiments, the third light device includes a third housing and a third plurality of lights arranged and configured to emit at least one of red light, blue light, green light, and/or near infrared light. Accordingly, in some embodiments the fourth light device includes a fourth housing and a fourth plurality of lights arranged and configured to emit at least one of red light, blue light, green light, and/or near infrared light. Similarly, in some embodiments the fifth light device includes a fifth housing and a fifth plurality of lights arranged and configured to emit at least one of red light, blue light, green light, and/or near infrared light. Finally, some embodiments include the sixth light device, which includes a sixth housing and a sixth plurality of lights arranged and configured to emit at least one of red light, blue light, green light, and/or near infrared light. Additionally, some embodiments include a first bracket arranged and configured to be detachably coupled to a back side of the first housing, a back side of the second housing, and a back side of the fifth housing to thereby detachably couple the first light device, second light device, and fifth light device together. Accordingly, some embodiments include a second bracket arranged and configured to be detachably coupled to a back side of the third housing, a back side of the fourth housing, and a back side of the sixth housing to thereby detachably couple the third light device, fourth light device, and sixth light device together. Additionally, some embodiments include a large bracket arranged and configured to be detachably coupled to the back side of the first housing, the back side of the second housing, the back side of the third housing, the back side of the fourth housing, the back side of the fifth housing, and the back side of the sixth housing to thereby detachably couple the first light device, second light device, third light device, fourth light device, fifth light device, and sixth light device together. In some embodiments, the large bracket is arranged and configured to be detachably coupled to a mobile stand.

In some embodiments, the system further includes the mobile stand having at least one vertical arm arranged and configured to couple to the large bracket. Additionally, in some embodiments, the mobile stand includes at least one horizontal leg arranged and configured to contact a floor surface.

In some embodiments, the first light device is a first modular light device and the second light device is a second modular light device whereby each of the first and second modular light devices are arranged and configured to be mechanically coupled in at least one of a side-by-side orientation and a top-to-bottom orientation. Furthermore, in some embodiments, the system includes a third modular light device and a fourth modular light device each arranged and configured to be mechanically coupled to at least one of the first, second, third, and fourth modular light devices in at least one of a side-by-side orientation and a top-to-bottom orientation.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

DETAILED DESCRIPTION

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any system or method disclosed herein, the acts or operations of the system or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Introduction

Photobiomodulation therapy provides an alternative option for treating many common ailments and diseases. For example, when the human body is exposed to red light, blue light, green light, and/or near infrared light, subjects can expect to see improvement in multiple skin conditions, weight loss, muscle recovery, sexual performance, joint pain, and thyroid function. Instead of using prescription medications to solve these many problems, light therapy can be used in place of these traditional remedies to achieve safe and effective results.

Light therapy has been adopted by many top professionals, but oftentimes the light therapy devices and systems used are not big enough to treat an entire body at once. Accordingly, many embodiments described herein enable two or more light therapy devices to be coupled together in various ways. In doing so, the area of treatment can be expanded to reduce the time and number of treatments to achieve the desired results.

Electrical Coupling Embodiments

Figure 1:
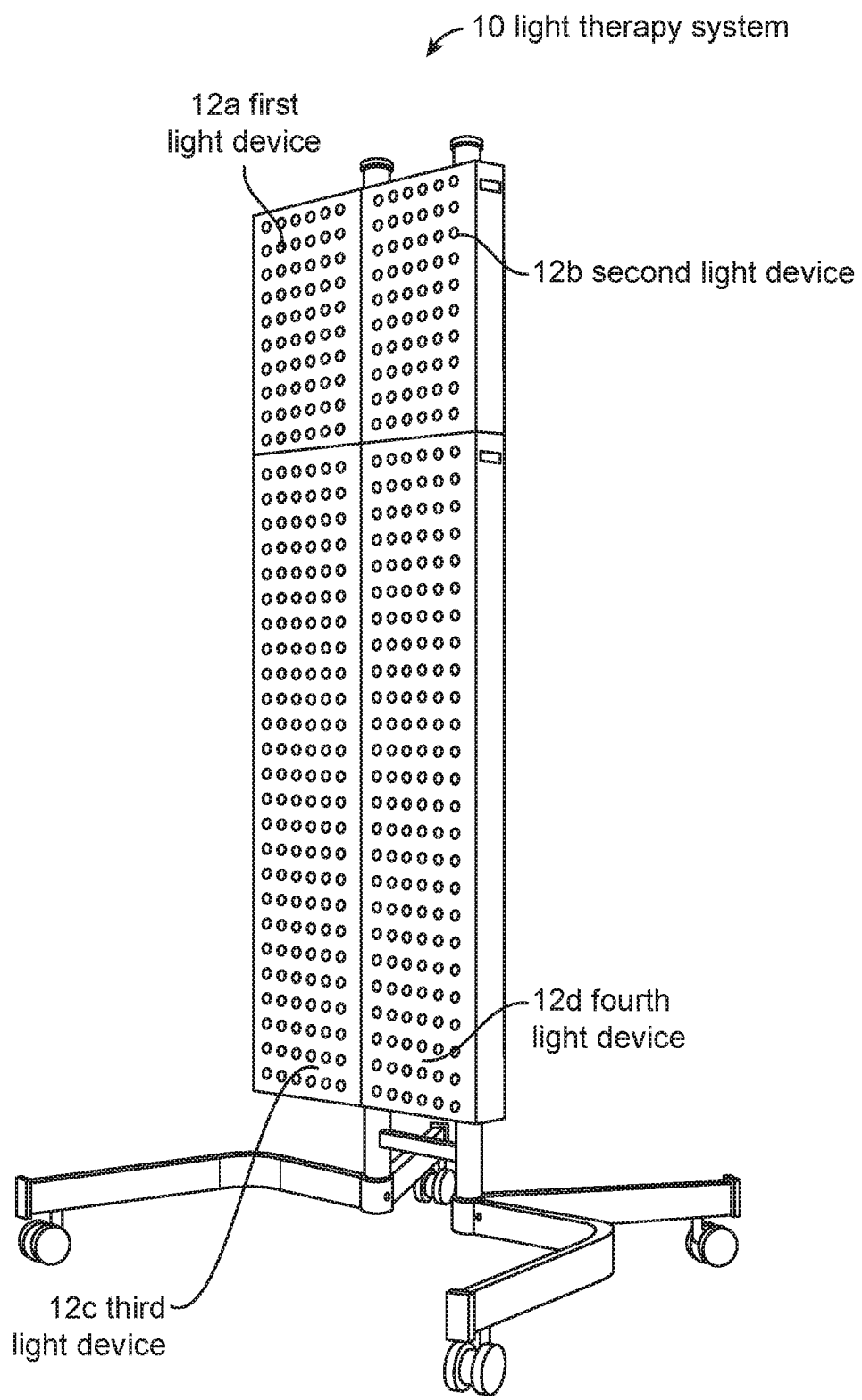
FIG. 1 illustrates a perspective view of an embodiment of a light therapy system.

The disclosure includes a light therapy system 10 that includes two or more light devices 12. For example, in some embodiments as shown in FIG. 1, the system 10 includes four light devices, such as a first light device 12a, a second light device 12b, a third light device 12c, and a fourth light device 12d. As will be shown and described, the four light devices 12 may be electrically and mechanically coupled together. The light therapy system 10 may further include an auxiliary mounting device, such as a mobile stand and/or a door stand, to assist in transporting and positioning the system 10.

Figure 2:
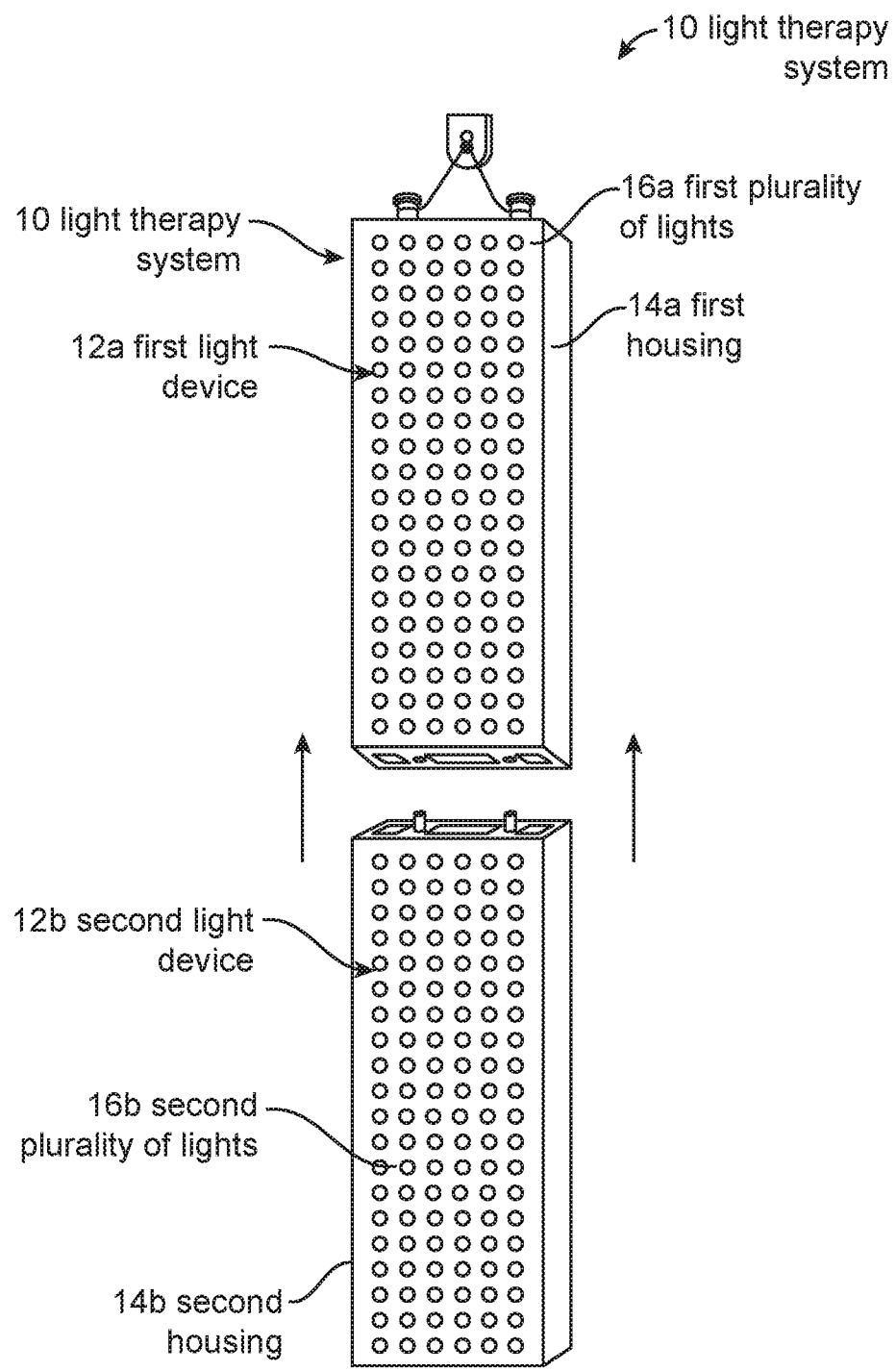
FIG. 2 illustrates a perspective view of a light therapy system, specifically how a first housing mechanically couples with a second housing.

In order to describe specific features and components of the light therapy system 10, we now refer to FIG. 2, which illustrates a perspective view of an embodiment of a system 10. As shown, the system 10 may include a first light device 12a comprising a first housing 14a and a first plurality of lights 16a, and a second light device 12b comprising a second housing 14b and a second plurality of lights 16b. The second light device 12b may be arranged and configured to couple to the first light device 12a. Both the first plurality of lights 16a and the second plurality of lights 16b are arranged and configured to emit red light, blue light, green light, and/or near infrared light. In some embodiments, the plurality of lights 16a and 16b may comprise a plurality of light emitting diodes (LED). Although LEDs are specifically mentioned herein, any light source capable of emitting red light, blue light, green light, and/or near infrared light may be appropriate. Furthermore, each light of the plurality of lights may be configured to emit both red light, blue light, green light, and/or near infrared light, or each light may be configured to only emit red light, blue light, green light, and/or near infrared light.

Figure 3:
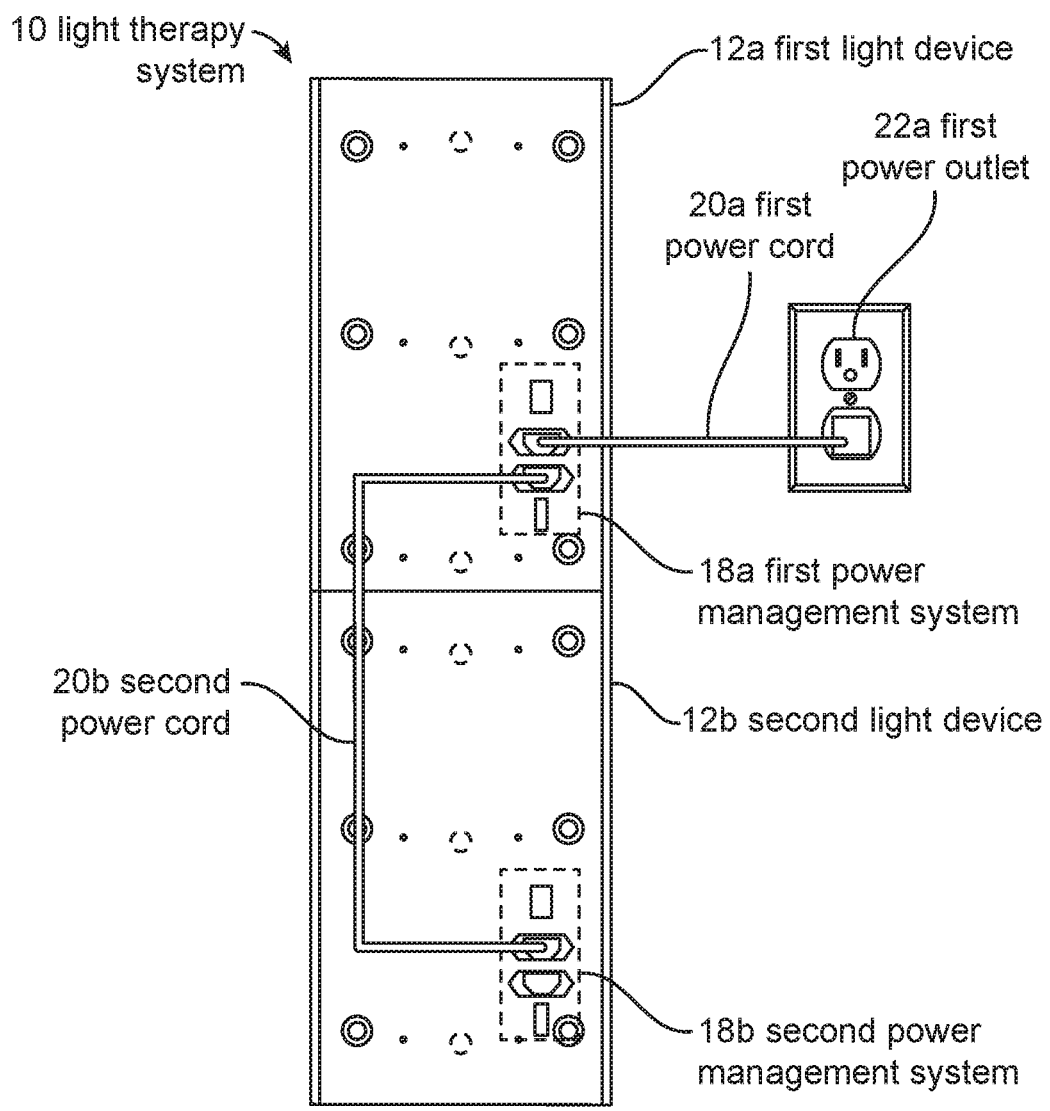
FIG. 3 illustrates a back view of a light therapy system, specifically how a first light device electrically couples with a second light device.

In some embodiments, the first light device 12a is arranged and configured to electrically couple to the second light device 12b. FIG. 3 illustrates one embodiment of how this may be achieved. The first light device 12a may comprise a first power management system 18a, which is electrically coupled to the first plurality of lights 16a. Likewise, the second light device 12b may comprise a second power management system 18b, which is electrically coupled to the second plurality of lights 16b. In some embodiments, the power management systems 18 may include an input port configured to receive a cord to thereby transfer power into the light devices 12, and an output port configured to transfer power out of the light device 12.

FIG. 3 further illustrates an embodiment which has a first power cord 20a electrically coupled to the first power management system 18a and a first power outlet 22a. Furthermore, FIG. 3 illustrates a second power cord 20b electrically coupled to the second power management system 18b. In such embodiments, power may pass through the first light device 12a via the second power cord 20b such that the second light device 12b will have sufficient power to perform as expected.

The power cord(s) 20 may also be configured to send signals from one light device 12 to another. This can be advantageous to ensure that multiple light devices 12 perform the same task. For example, a user may wish to use only red light, blue light, green light, and/or near infrared light, or any combination of lights. In some embodiments, a user may input instructions into the first light device 12a, and the signal will be carried through by the second power cord 20*b* to the second light device 12*b*. In this regard, the second light device 12*b* will be paired to the first light device 12*a*.

Figure 4:
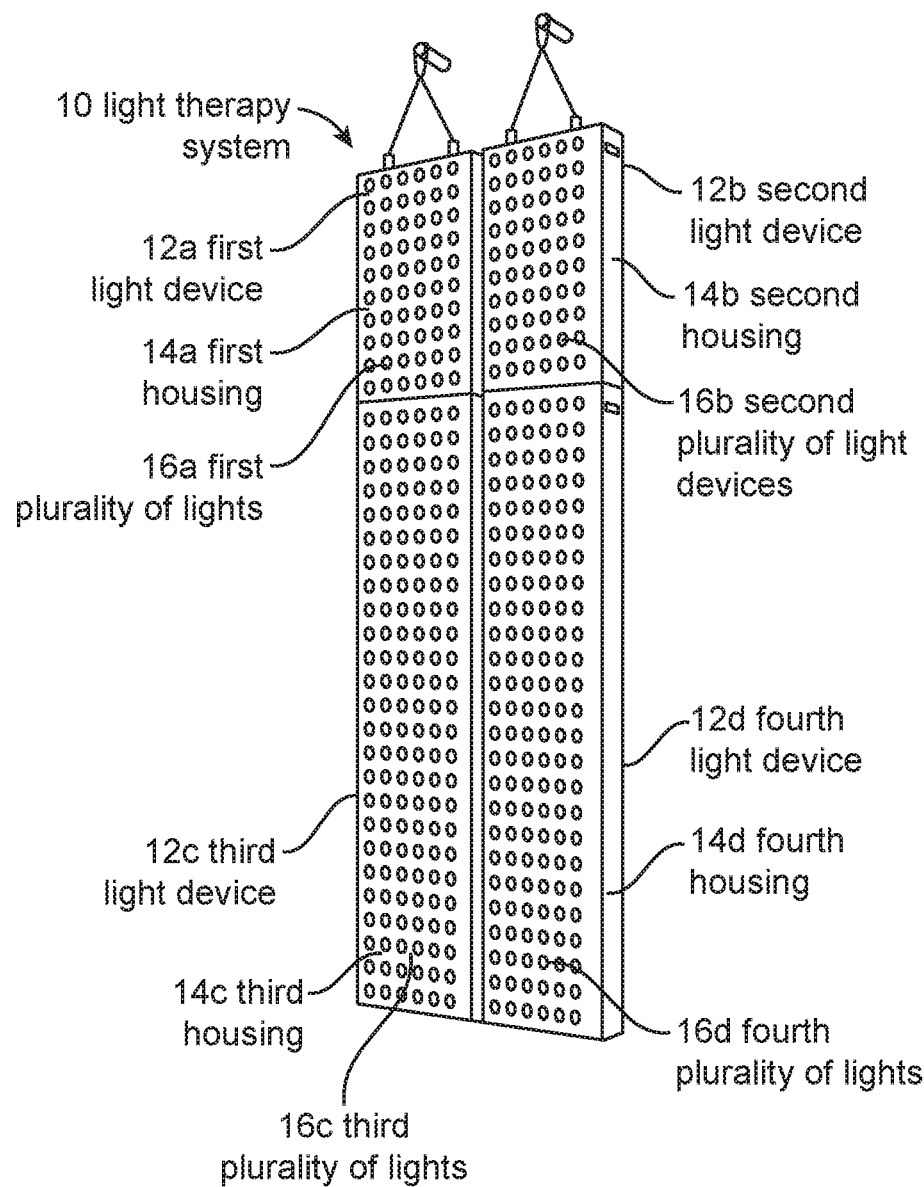
FIG. 4 illustrates a perspective view of a light therapy system having four light devices mechanically coupled.
Figure 5:
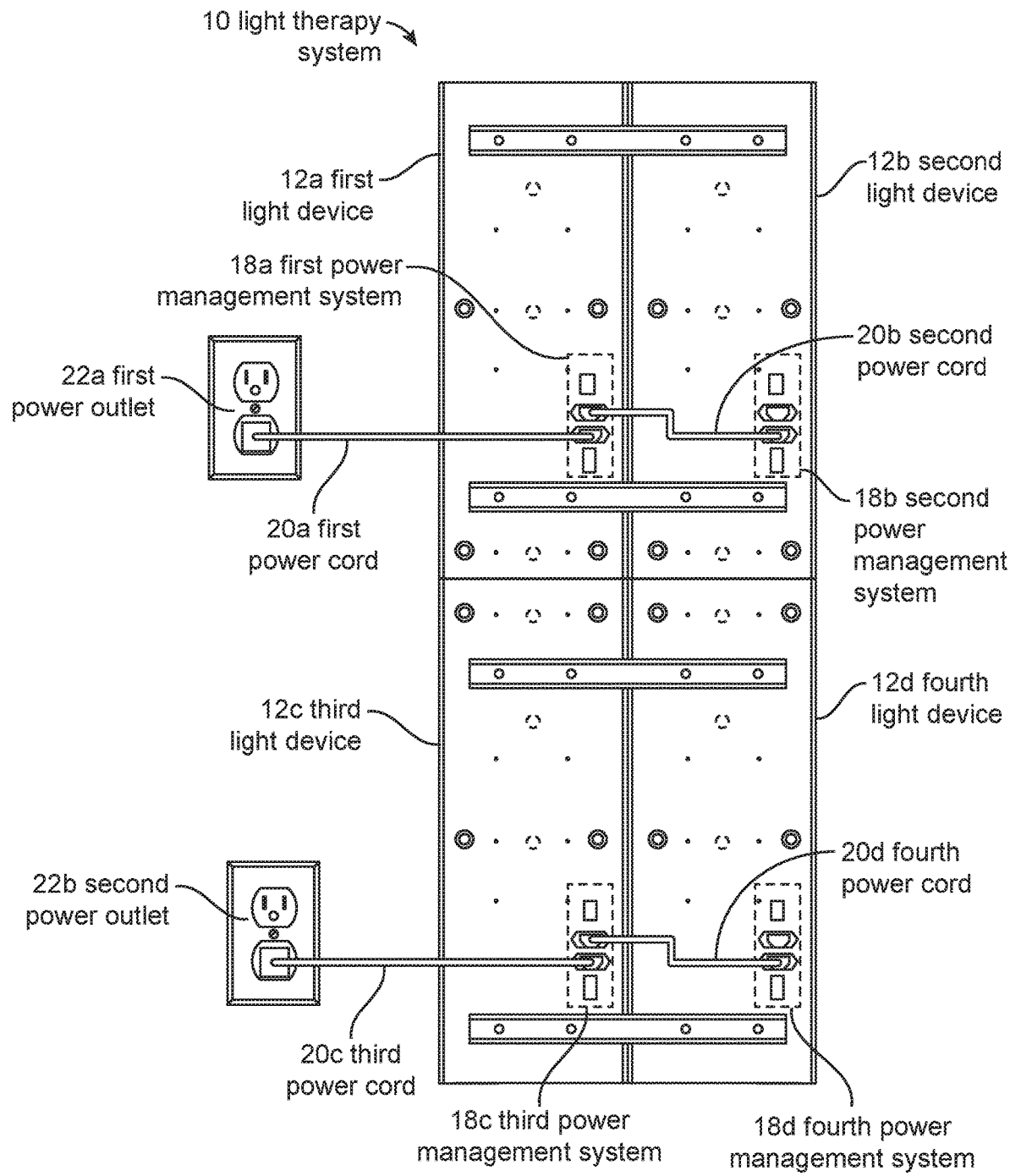
FIG. 5 illustrates a back view of a light therapy system in which a first light device is electrically coupled to a first power outlet and a second light device, and a third light device electrically coupled to a second power outlet and a fourth light device.

Some treatments may require a larger therapy area than that provided by two light devices. Accordingly, FIG. 4 illustrates a perspective view of an embodiment which comprises, in addition to the first light device 12*a* and the second light device 12*b*, a third light device 12*c* configured to be electrically coupled with the first light device 12*a* and/or the second device 12*b*. The third light device 12*c* may comprise a third housing 14*c*, a third plurality of lights 16*c*, and a third power management system 18*c* (FIG. 5). The embodiment depicted in FIG. 4 also shows a fourth light device 12*d* configured to be coupled with any one of the first light device 12*a*, second light device 12*b*, and/or the third light device 12*c*. The fourth light device 12*d* may also comprise a fourth housing 14*d*, a fourth plurality of lights 16*d*, and a fourth power management system 18*d* (FIG. 5). The third plurality of lights 16*c* and the fourth plurality of lights 16*d* may also be configured to emit red light, blue light, green light, and/or near infrared light.

The light therapy system 10 may be arranged in a variety of electrical configurations, whereby light devices 12 are electrically coupled in series. Specifically, FIGS. 5, 6, 8, and 9 illustrate two different scenarios of how the system 10 may be coupled. With respect to FIGS. 5 and 8, the system 10 may be electrically coupled in series having a maximum number of three light devices 12 per series. In other words, three light devices may be electrically coupled in series to a power outlet 22. Because there are four light devices 12 in FIG. 5, the configuration thereby requires two power outlets 22*a* and 22*b*. As such, following the discussion with respect to FIG. 3, a third power cord 20*c* may be electrically coupled to a third power management system 18*c* and a second power outlet 22*b*. As well, a fourth power cord 20*d* may be electrically coupled to the third power management system 18*c* and a fourth power management system 18*d*. In this regard, the second and fourth light devices 12*b*, 12*d* may thereby receive electrical power from the first and third light devices 12*a*, 12*c*, respectively, which in turn receive electrical power from the first and second power outlets 22*a*, 22*b*, respectively.

Figure 6:
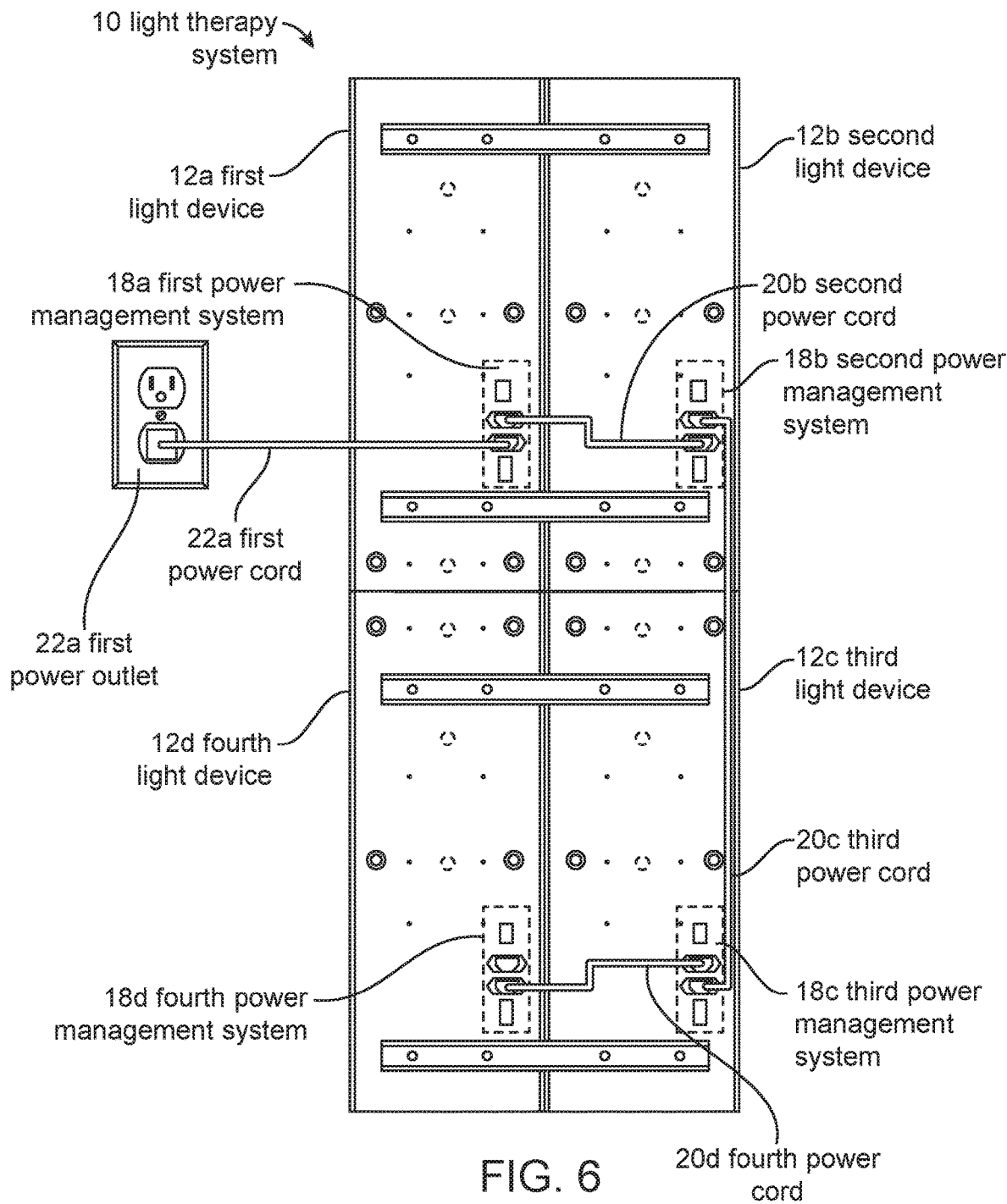
FIG. 6 illustrates a back view of a light therapy system in which a first light device is electrically coupled to a first power outlet and a second light device, the second light device is also electrically coupled to a third light device, and the third light device is also electrically coupled to a fourth light device.
Figure 9:
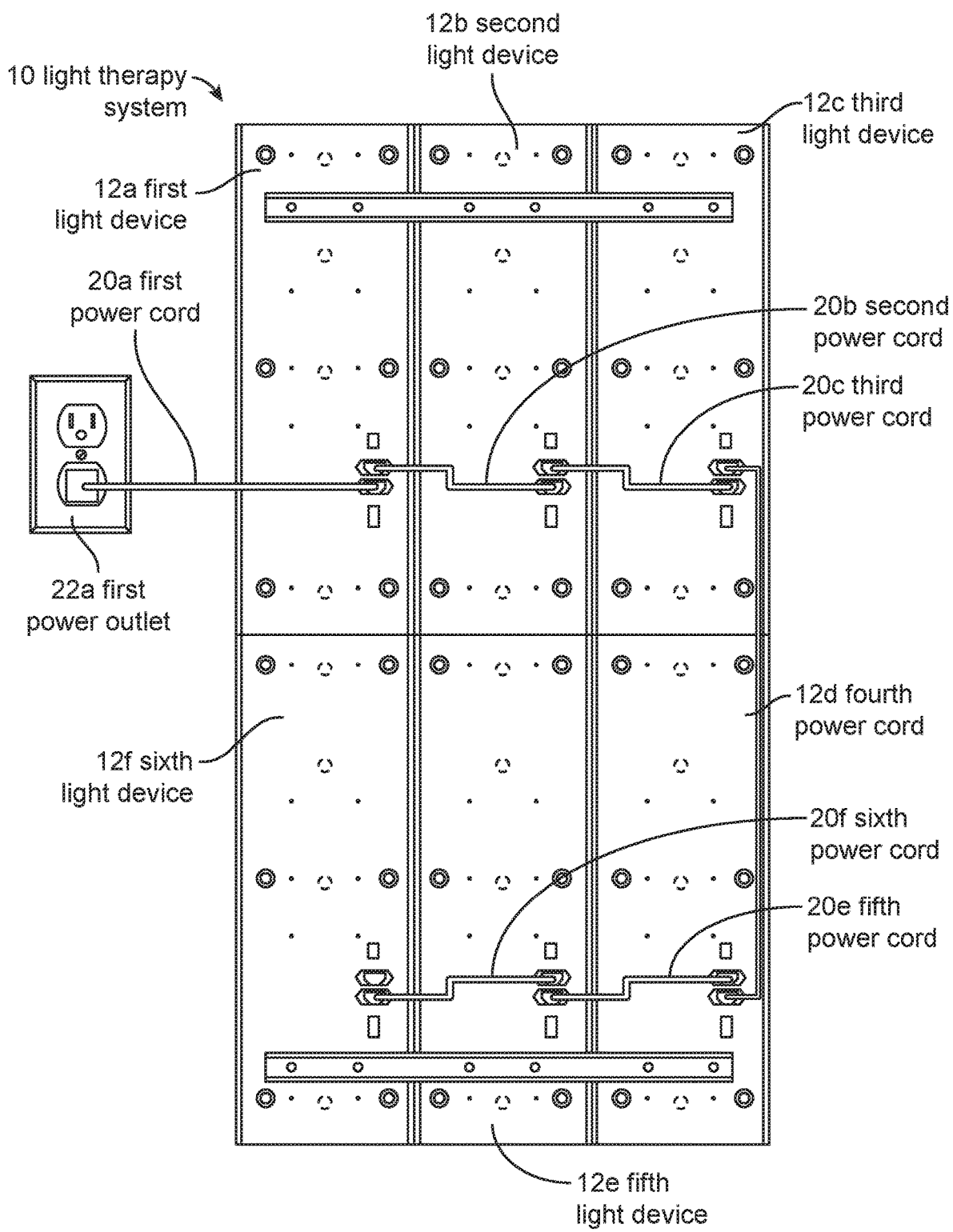
FIG. 9 illustrates a back view of another light therapy system, specifically showing six light devices mechanically and electrically coupled together.

Now, with respect to FIGS. 6 and 9, some embodiments may be configured with no limit on the number of light devices 12 electrically coupled in series. Again, building from the configuration disclosed with respect to FIG. 3, the third power cord 20*c* may be electrically coupled to the second power management system 18*b* and the third power management system 18*c*. The fourth power cord 28*d* may be electrically coupled to the third power management system 18*c* and the fourth power management system 18*d*. Coupling the third power cord 18*c* in this way removes the need for the second power outlet 22*b*. This configuration may be advantageous depending on the power requirements of the light therapy system 10. For example, smaller light devices may require less power to achieve the desired outcome. However, a larger light device may require a great deal more power than only one power outlet can provide.

Figure 7:
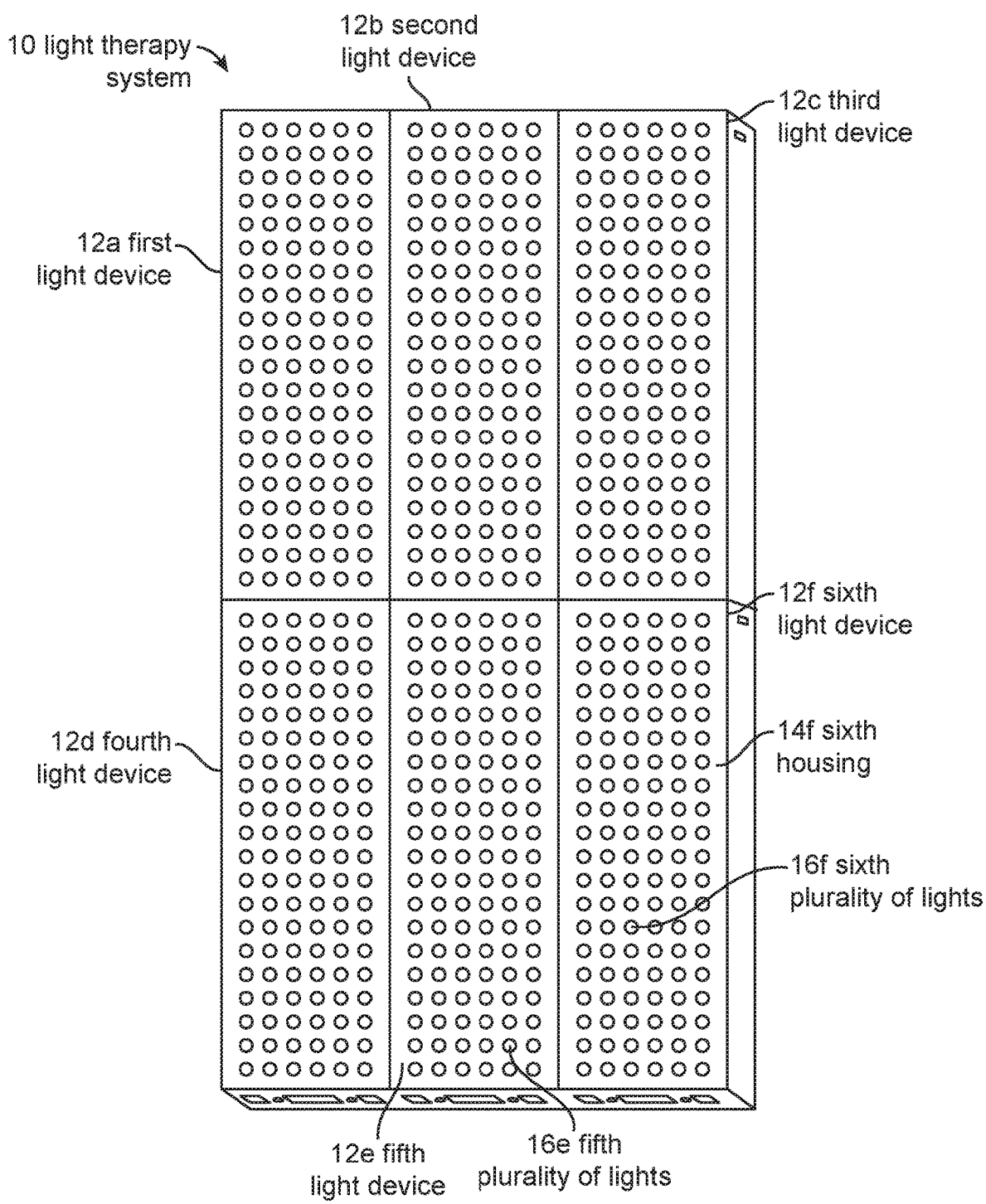
FIG. 7 illustrates a perspective view of a light therapy system having six light devices mechanically coupled together.
Figure 8:
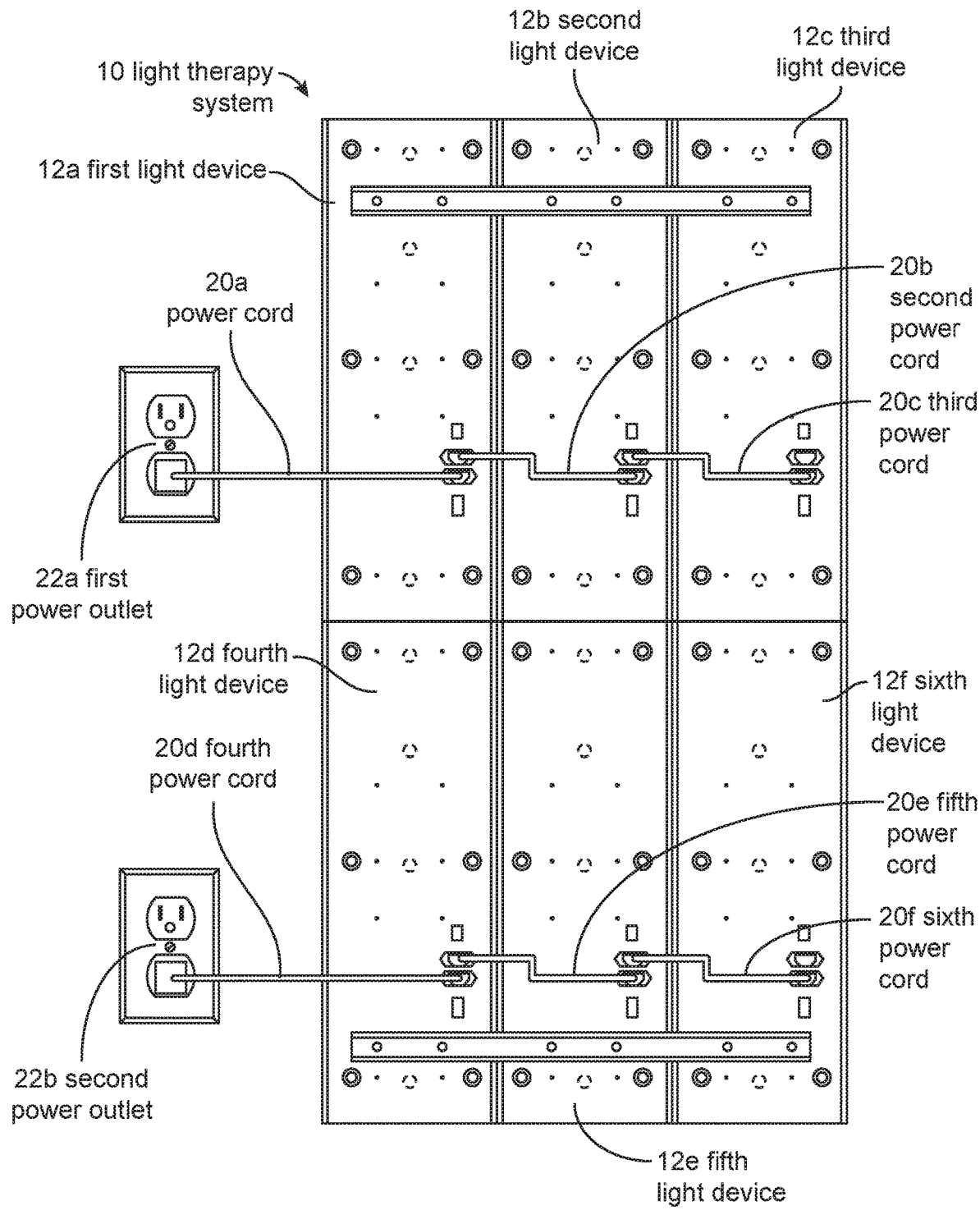
FIG. 8 illustrates a back view of a light therapy system, specifically showing six light devices mechanically and electrically coupled together.

FIGS. 7, 8, and 9 depict how some embodiments of a light therapy system 10 may be further expanded from four to six light devices and how the light devices may be electrically coupled to provide necessary power. As illustrated, a fifth light device 12*e* may be coupled to the any one of the first, second, third, or fourth light devices 12*a*, 12*b*, 12*c*, 12*d*. The fifth light device 12*e* may comprise a fifth housing 14*e*, a fifth plurality of lights 16*e*, and a fifth power management system 18*e*. The fifth power management 18*e* system may be electrically coupled with the fifth plurality of lights 16*e*. A sixth light device 12*f* may be configured to be coupled to any one of the first, second, third, fourth, or fifth light devices 12*a*, 12*b*, 12*c*, 12*d*, 12*e*. The sixth light device 12*f* may comprise a sixth housing 14*f*, a sixth plurality of lights 16*f*, and a sixth power management system 18*f*. The sixth power management 18*f* system may be electrically coupled with the sixth plurality of lights 16*f*. It should be appreciated that the plurality of lights 16*e* and 16*f* are configured to emit red light, blue light, green light, and/or near infrared light.

Revisiting the manner in which the light devices 12 may be electrically coupled in series we now refer to FIG. 8, which illustrates a light therapy system 10 having six light devices 12*a*, 12*b*, 12*c*, 12*d*, 12*e*, and 12*f*. Because the embodiment illustrated in FIG. 8 is limited to three devices in series, the system 10 thereby requires two power outlets 22*a*, 22*b*. Continuing with the discussion from FIG. 5, the fourth power cord 20*d* may be electrically coupled to the fourth power management system 18*d* and the second power outlet 22*b*. A fifth power cord 20*e* may be electrically coupled to the fourth power management system 18*d* and the fifth power management system 18*e*. The sixth power cord 20*f* may be electrically coupled to the fifth power management system 18*e* and the sixth power management system 18*f*. In this embodiment the first through third light devices 12*a*, 12*b*, and 12*c* are connected in a first series, and the fourth through sixth light devices 12*d*, 12*e*, and 12*f* are connected in a second series.

As well, FIG. 9 shows another embodiment in which all the light devices 12*a*, 12*b*, 12*c*, 12*d*, 12*e*, and 12*f* are all connected in one series. Continuing with the discussion from FIG. 6, the fourth power cord 20*d* may be electrically coupled to the third power management system 18*c* and the fourth power management system 18*d*. The fifth power cord 20*e* may be electrically coupled to the fourth power management system 18*d* and the fifth power management system 18*e*. The sixth power cord 20*f* may thereby be electrically coupled to the fifth power management system 18*e* and the sixth power management system 18*f*. Configuring the light therapy system 10 in this manner avoids the need for the second power outlet 22*b*.

Mechanical Coupling Embodiments

Figure 10:
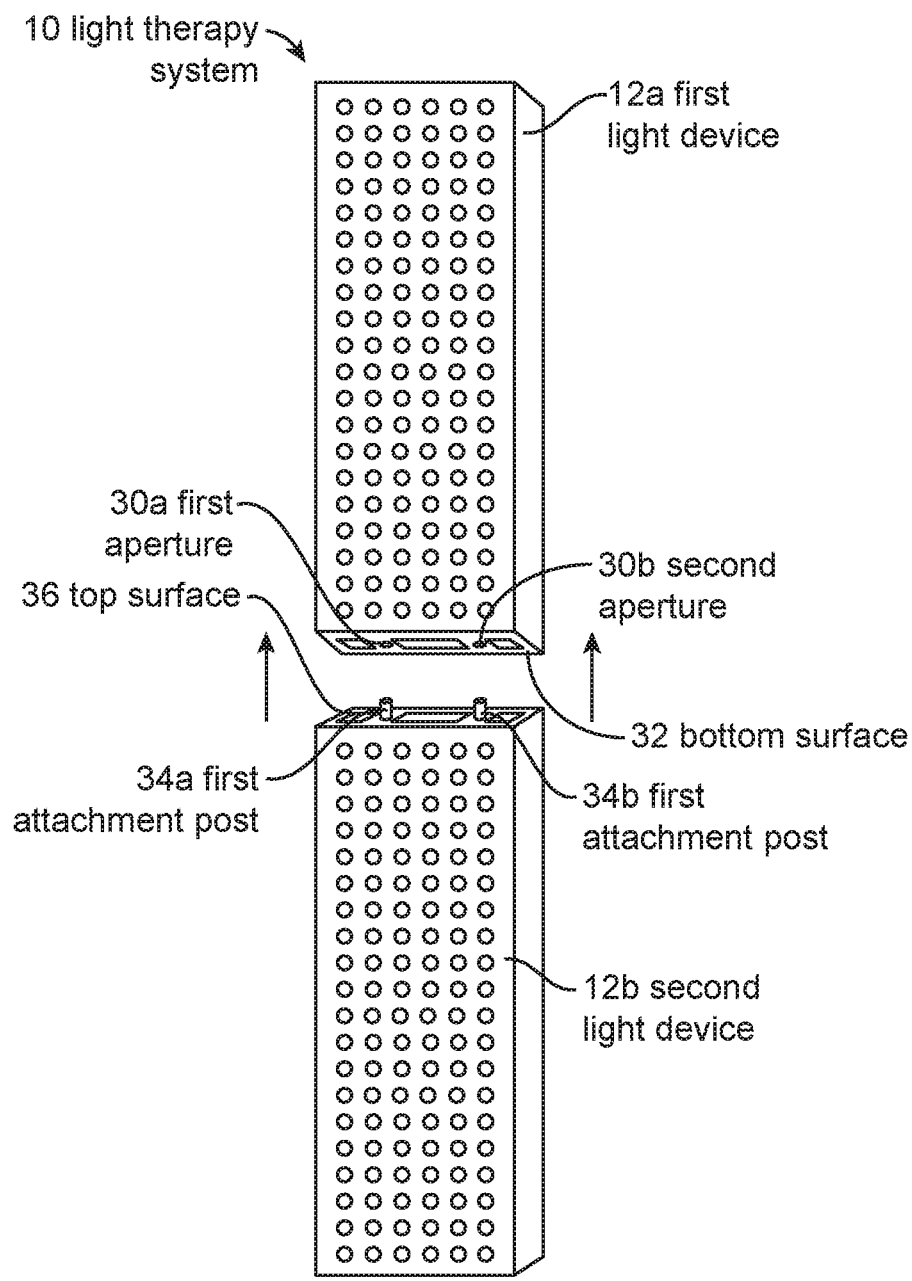
FIG. 10 illustrates a perspective view of a light therapy system in which a first light device is mechanically coupled with a second light device in a top-to-bottom orientation.

The disclosure also includes embodiments whereby multiple light devices 12 are mechanically coupled together to form a variety of light system sizes and configurations. In doing so, mechanical coupling allows the light devices 12 to work together, as a system, to create one large treatment area. FIG. 10 illustrates an embodiment of how two light devices 12 may be configured for mechanical coupling in a top-to-bottom orientation. The light therapy system 10 of FIG. 10 comprises a first aperture 30*a* and a second aperture 30*b* located on the bottom surface 32 of the first housing 14*a*. A first attachment member 34*a* and a second attachment member 34*b* are located on the top surface 36 of the second housing 14*b*. The attachment members 34 may be thereby securely fit into the apertures 30 to mechanically couple the light devices 12 together. The attachment members 34 shown in FIG. 10 are posts, but any mechanism suitable for mechanical coupling may be implemented. For example, light devices 12 may be mechanically coupled together via adhesive, bolts, and the like. It should be appreciated that the attachment members 34 are detachably coupled with the apertures 30 such that a user may detach the light devices 12 from one another.

Figure 11:
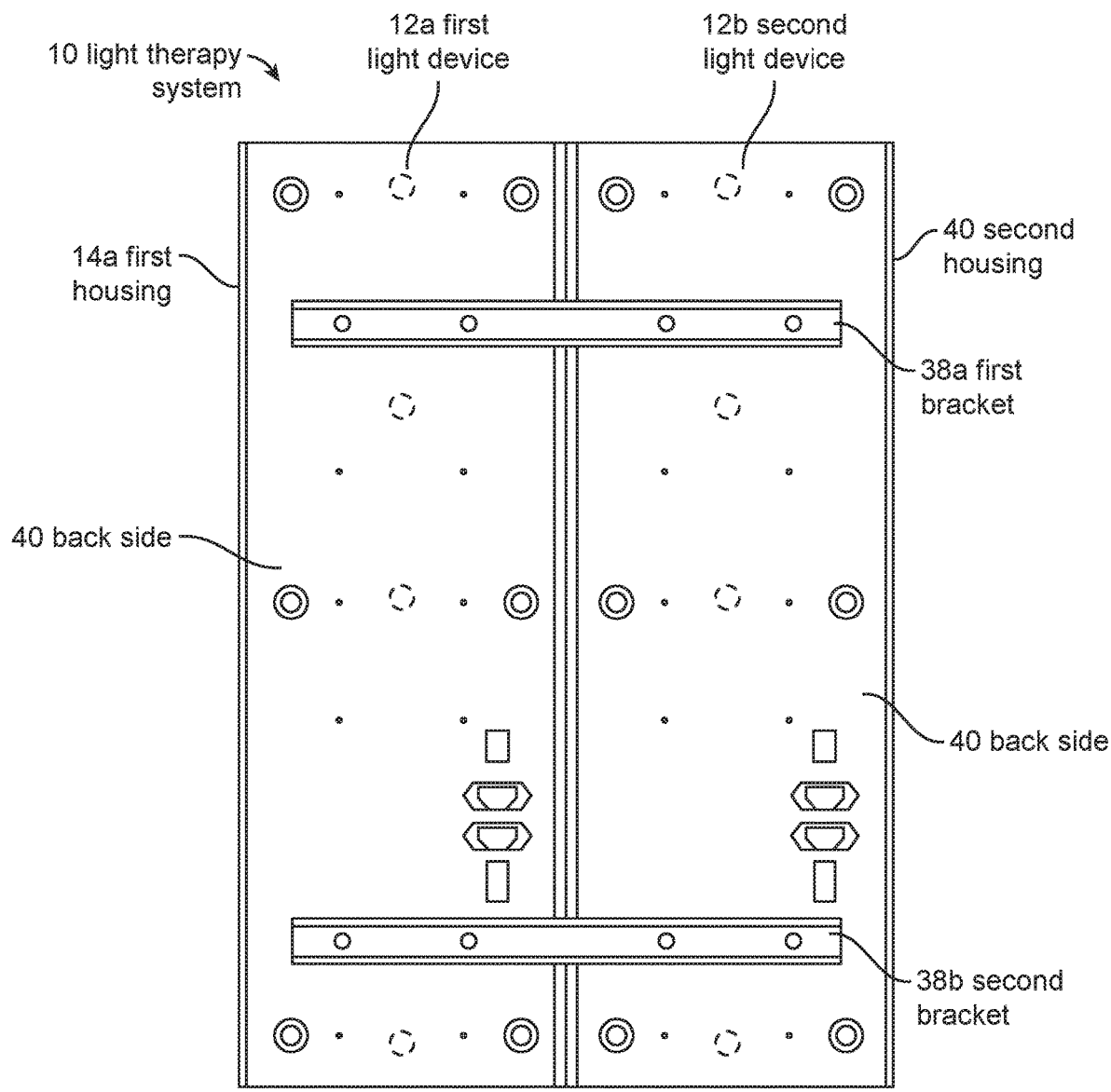
FIG. 11 illustrates a back view of a light therapy system in which a first light device is mechanically coupled to a second light device in a side-by-side orientation.

FIG. 11 depicts an embodiment of a light therapy system 10 in which two light devices 12 are mechanically coupled in a side-by-side orientation. The embodiment in FIG. 11 shows a first bracket 38a mechanically coupled to the back side 40 of the first and second light devices 12a and 12b. Similarly, a second bracket 38b is also mechanically coupled to the back side 40 of the first and second light devices 12a and 12b. It should be appreciated that the brackets 38 are detachably coupled to the light devices 12.

Figure 12:
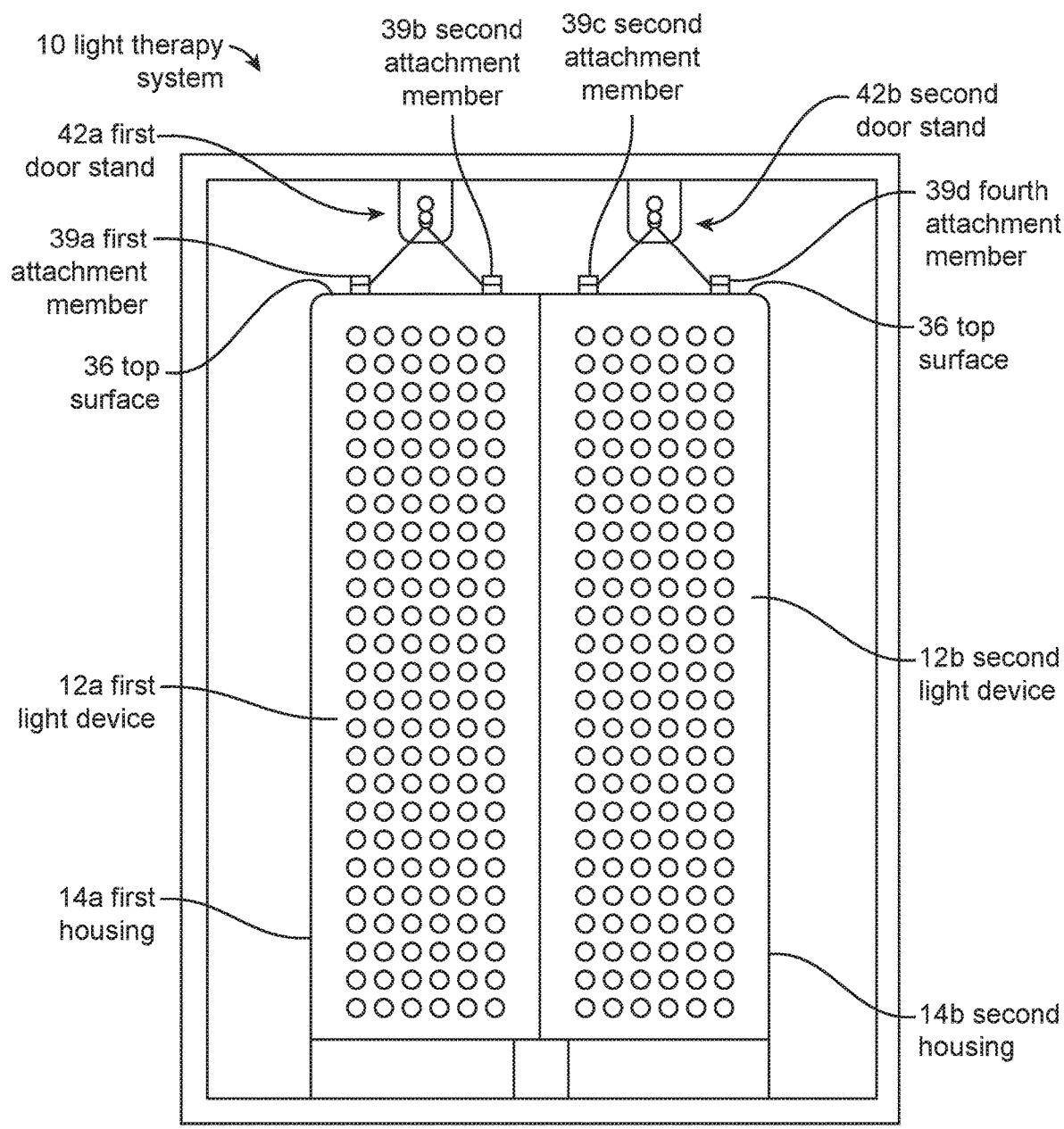
FIG. 12 illustrates a front view of a light therapy system that has four light devices mechanically coupled and is mounted to a door via a first and a second door stand.

It may be beneficial for the light therapy system 10 to be mounted to an auxiliary support, such as a door stand 42 or a mobile stand 50. This can be achieved in several ways. FIG. 12 shows one embodiment in which two light devices 12a and 12b are mechanically coupled in a side-by-side orientation and mounted to a first and a second door stand 42a and 42b. In doing so, a first attachment member 39a and a second attachment member 39b may extend from the top surface 36 and be detachably coupled to the first door stand 42a. Similarly, the second door stand 42b is detachably coupled to the third attachment member 39c and the fourth attachment member 39d.

Figure 13:
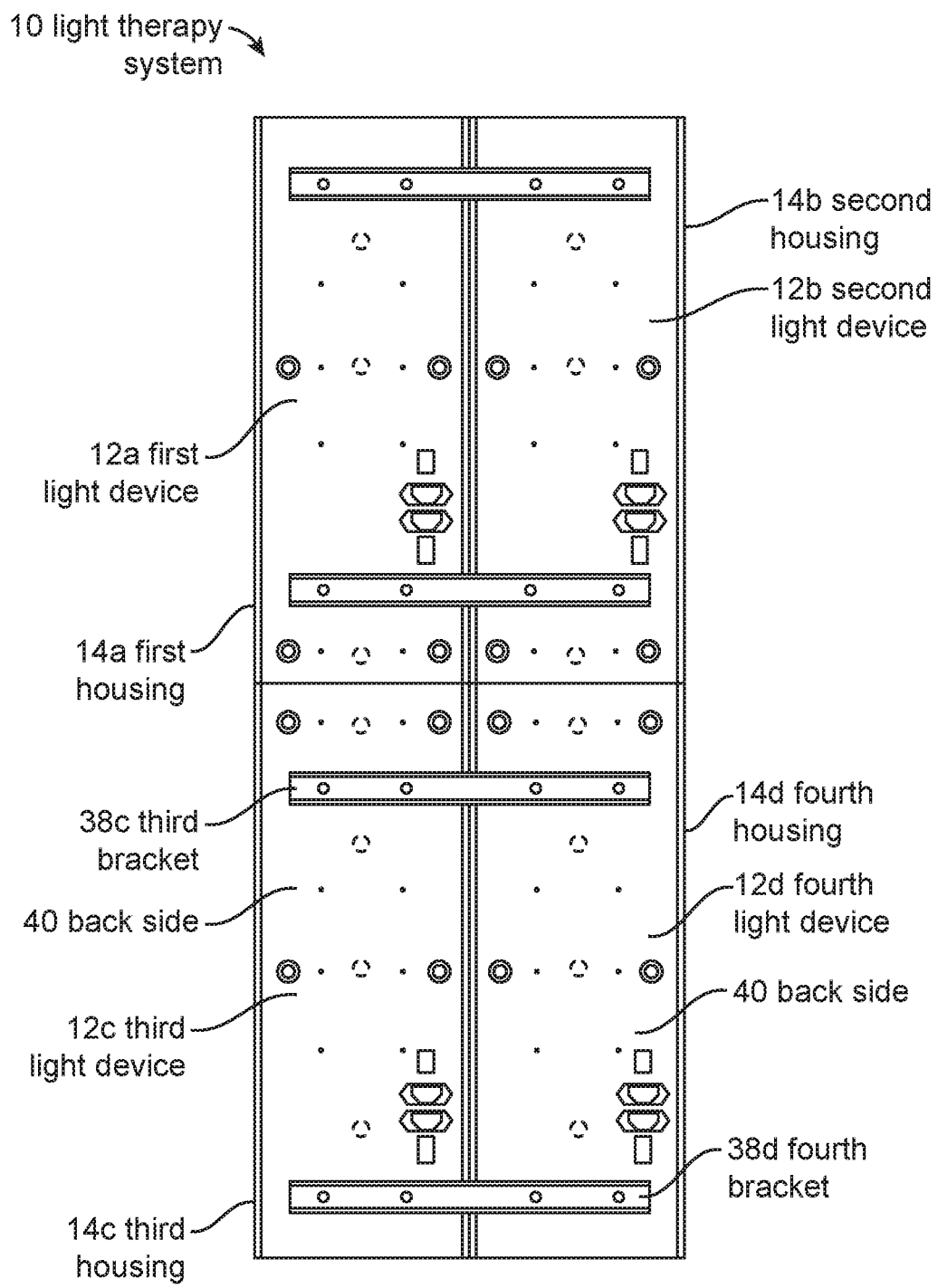
FIG. 13 illustrates a back view of a light therapy system in which a first light device is mechanically coupled to a second light device via a first and a second bracket, and a third light device is mechanically coupled to a fourth light device via a third and a fourth bracket.
Figure 14:
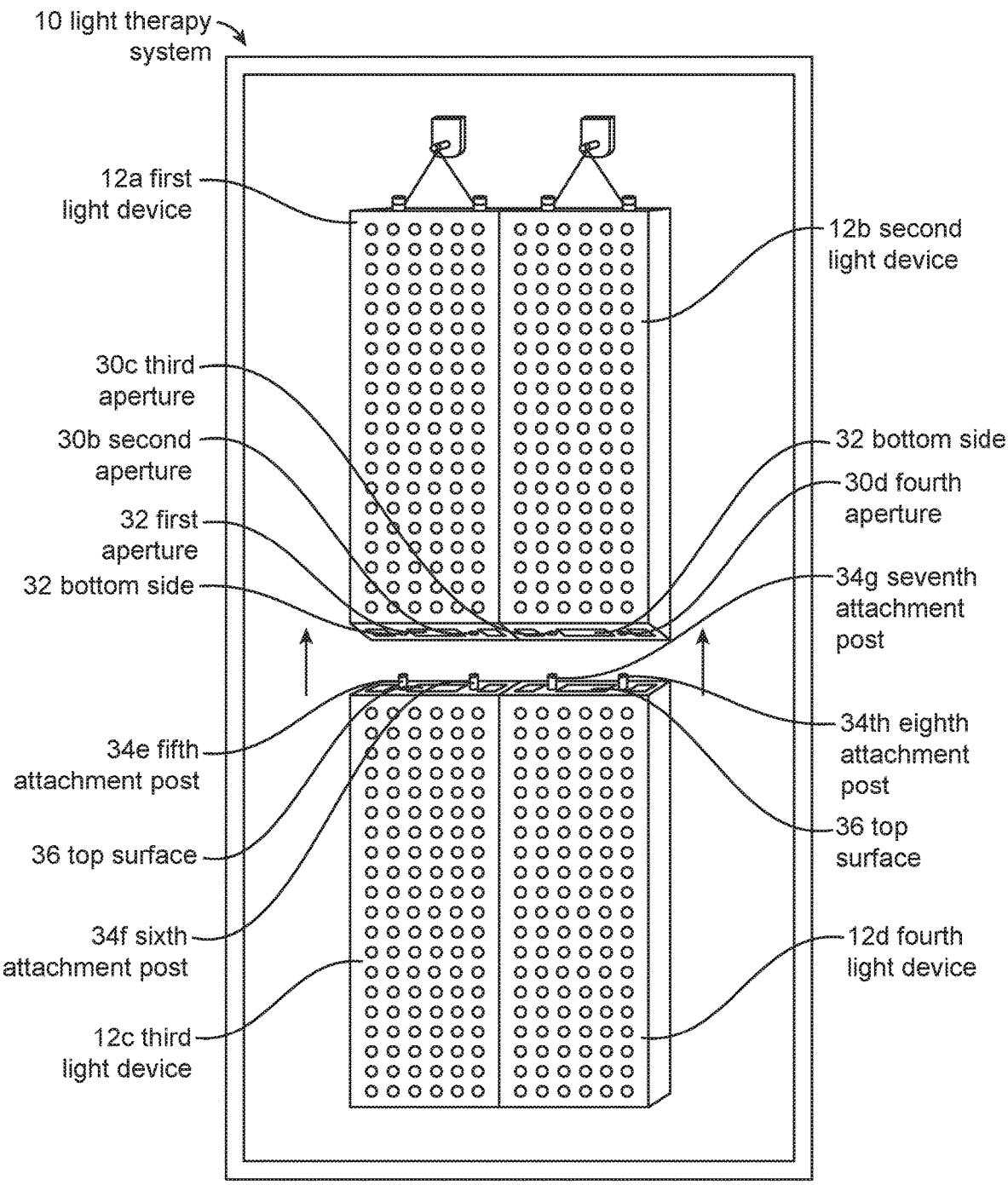
FIG. 14 illustrates a perspective view of a light therapy system mounted to a door, specifically showing a third and fourth housing mechanically coupled with a first and second housing.
Figure 15A:
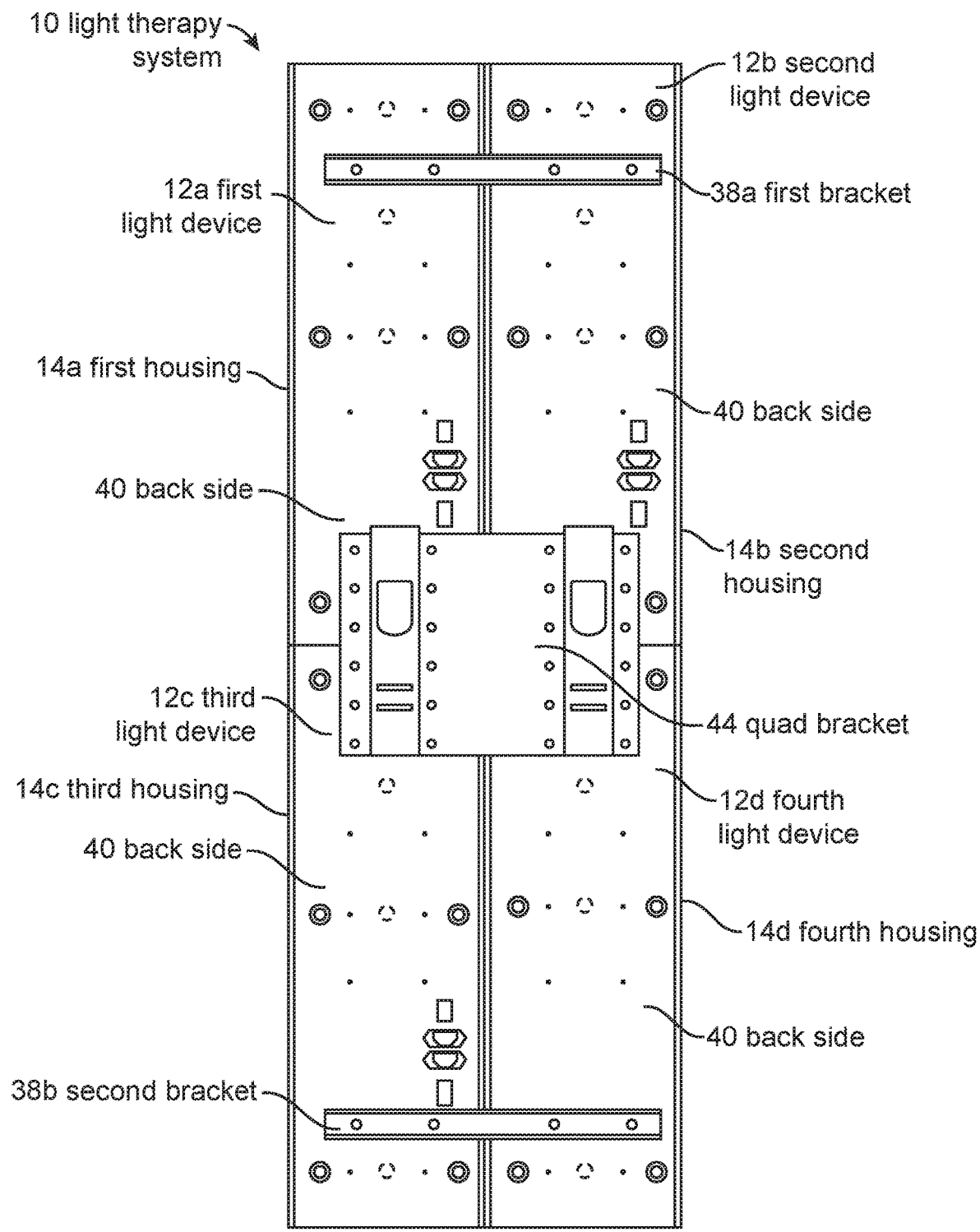
FIG. 15A illustrates a back view of a light therapy system in which first, second, third, and fourth light devices are mechanically coupled via a first bracket, a second bracket, and a quad bracket.
Figure 15B:
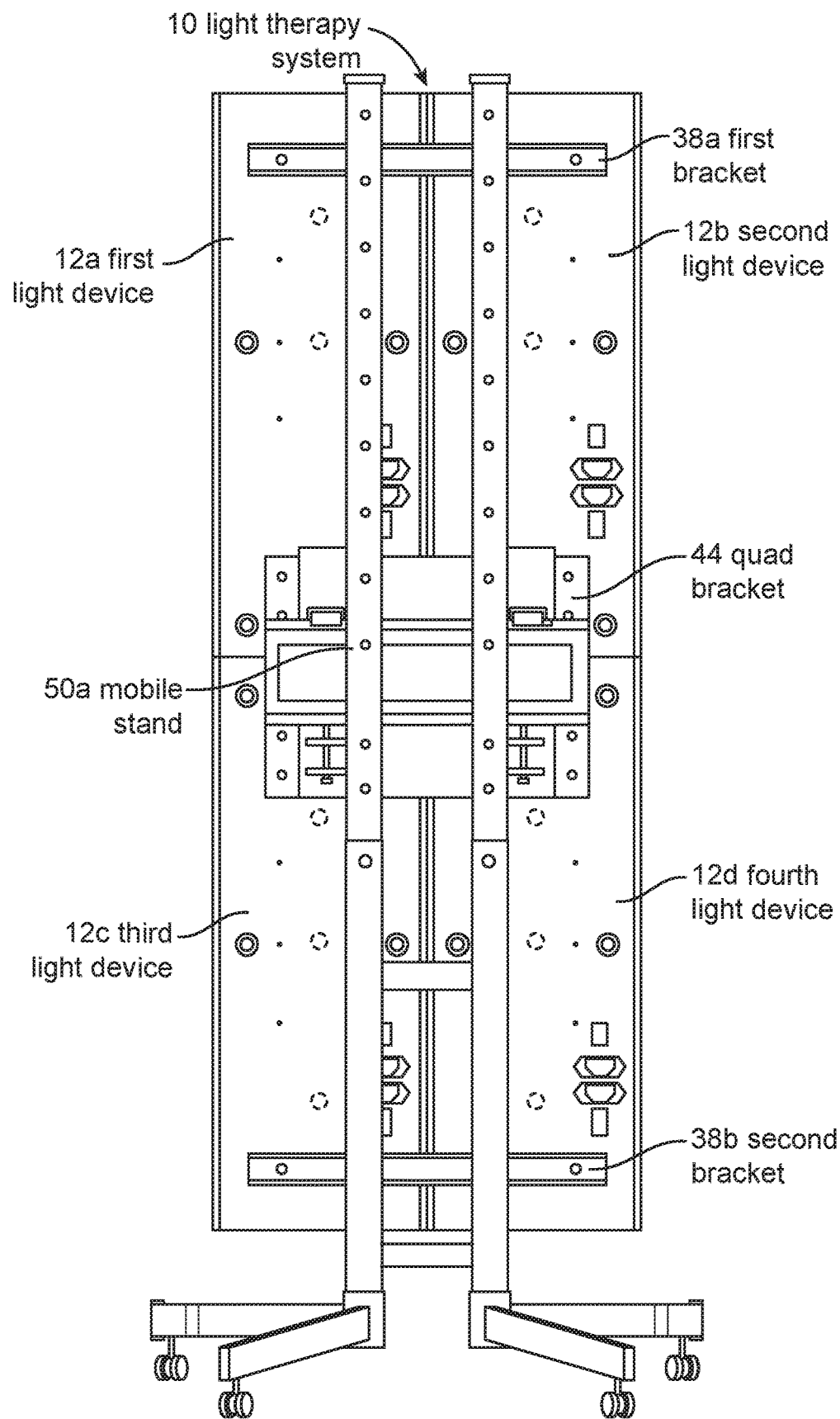
FIG. 15B illustrates a back view of a light therapy system in which first, second, third, and fourth light devices are mechanically coupled via a first bracket, a second bracket, and a quad bracket, whereby the quad bracket is mechanically coupled with a mobile stand.
Figure 15C:
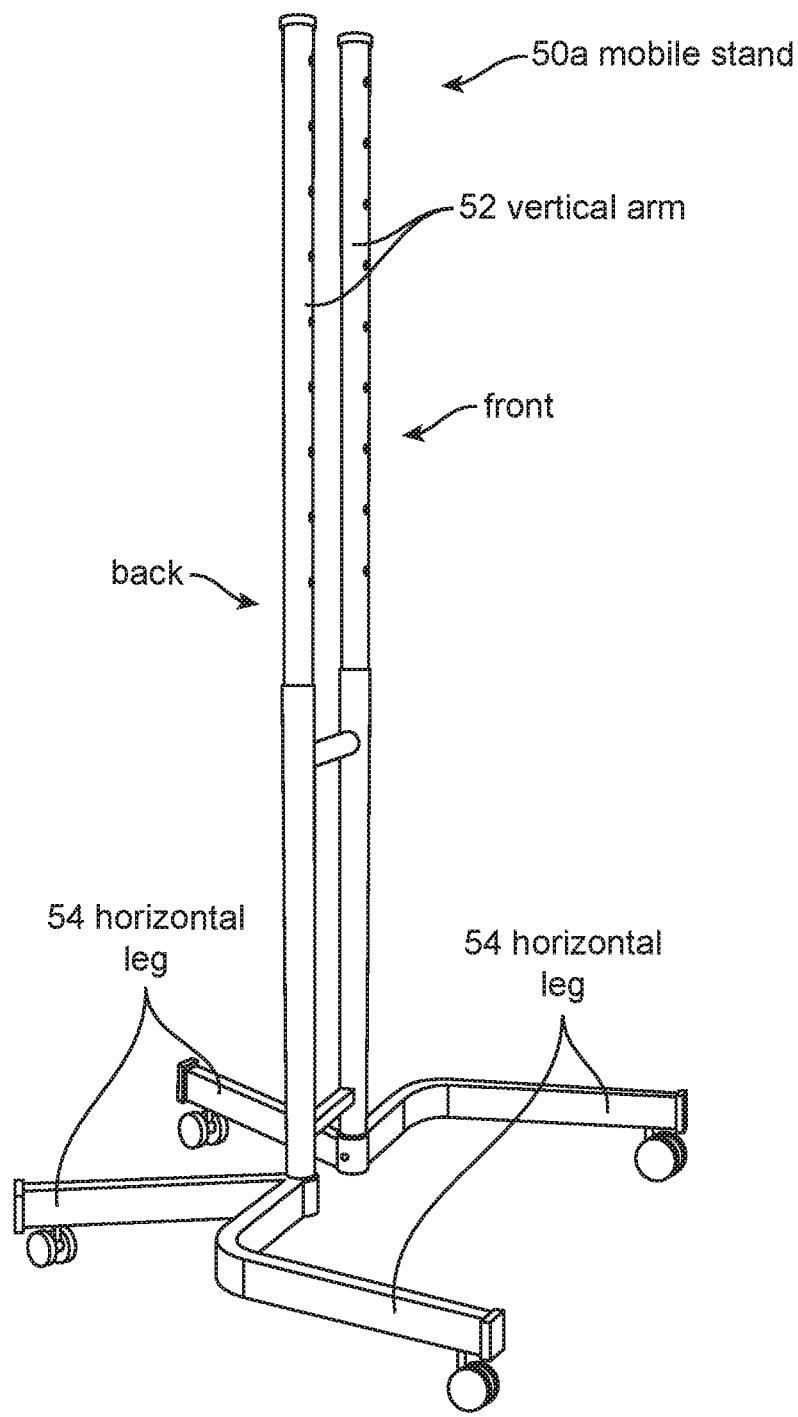
FIG. 15C illustrates a perspective view of a mobile stand.

FIGS. 13 and 14 show light therapy system 10 embodiments that combine the top-to-bottom coupling with the side-by-side coupling to achieve a two by two grid of light devices 12. FIG. 13 illustrates a third bracket 38c and a fourth bracket 38d coupled to the back side 40 of the third housing 14c and the fourth housing 14d. FIG. 14 illustrates a fifth attachment post 34e, a sixth attachment post 34f, a seventh attachment post 34g, and an eighth attachment post 34h coupled to the top surface 36 of the third light device 12c and the fourth light device 12d. The illustration in FIG. 14 further depicts the two by two grid of light devices 12 mounted to door stands 42.

In other embodiments, the four light devices 12 may be mechanically coupled together in other arrangements. For example, one embodiment may have all four light devices 12 coupled together in a side-by-side orientation forming a one by four grid. In other examples, three light devices 12 may be coupled together in a side-by-side orientation and the fourth light device 12d may be coupled to any one of the other three light devices 12 in a top-to-bottom orientation. Another possible embodiment may feature a four by one grid in which the four light devices 12 are all coupled in a top-to-bottom orientation. Generally, it should be appreciated that any arrangement or configuration of light devices may be achieved using the modular concepts disclosed herein.

Mounting Embodiments

In order to facilitate ease of using the light therapy system 10 and/or individual light device(s) 12, the disclosure also includes various devices for mounting the system 10 and/or light device(s) 12. For example, users may wish to mount the system 10 and/or device(s) 12 to a stand, such as a mobile stand 50, table top stand 59 (or mini stand 59), wall stand 58, and the like. A stand may thereby allow the system 10 and/or device(s) 12 to be easily transported from one place to another and then quickly configured in a variety of positions to effectively apply therapy to any treatment zone on a patient. Additionally, a stand may allow a user to set up the system 10 and/or light device 12 in an easy to access yet out of the way location, such as the wall stand 58.

Now with reference to the figures, as shown in FIGS. 15A-17, the light therapy system 10 includes a mobile stand 50 that couples to one or more brackets on the back side of the various light devices 12. With regard to the four light device embodiment, the first bracket 38a may be coupled the to the back side 40 of the first housing 14a and the second housing 14b and the second bracket 38b may be coupled to the back side 40 of the third housing 14c and the fourth housing 14d. A quad bracket 44 may thereby be coupled to the back side 40 of the first housing 14a, second housing 14b, third housing 14c, and the fourth housing 14d. Accordingly, the mobile stand 50 may be detachably coupled to the light devices 12, the bracket(s) 38, and/or quad bracket 44.

The mobile stand 50a may include one or more horizontal legs 54 to stabilize the system 10. The one or more horizontal legs 54 may include casters to make it easier for a user to move the mobile stand 50a. Casters are not necessary though, for example, wheels may be implemented instead. Even still, the horizontal legs 54 may not include casters or wheels at all, and the horizontal legs 54 may be affixed to a ground surface or not affixed and free to move with respect to the ground surface. In any case, the horizontal leg 54 may provide balance and stability to the mobile stand 50a. To achieve this, some part of the horizontal leg 54 may contact the ground surface.

Figure 17:
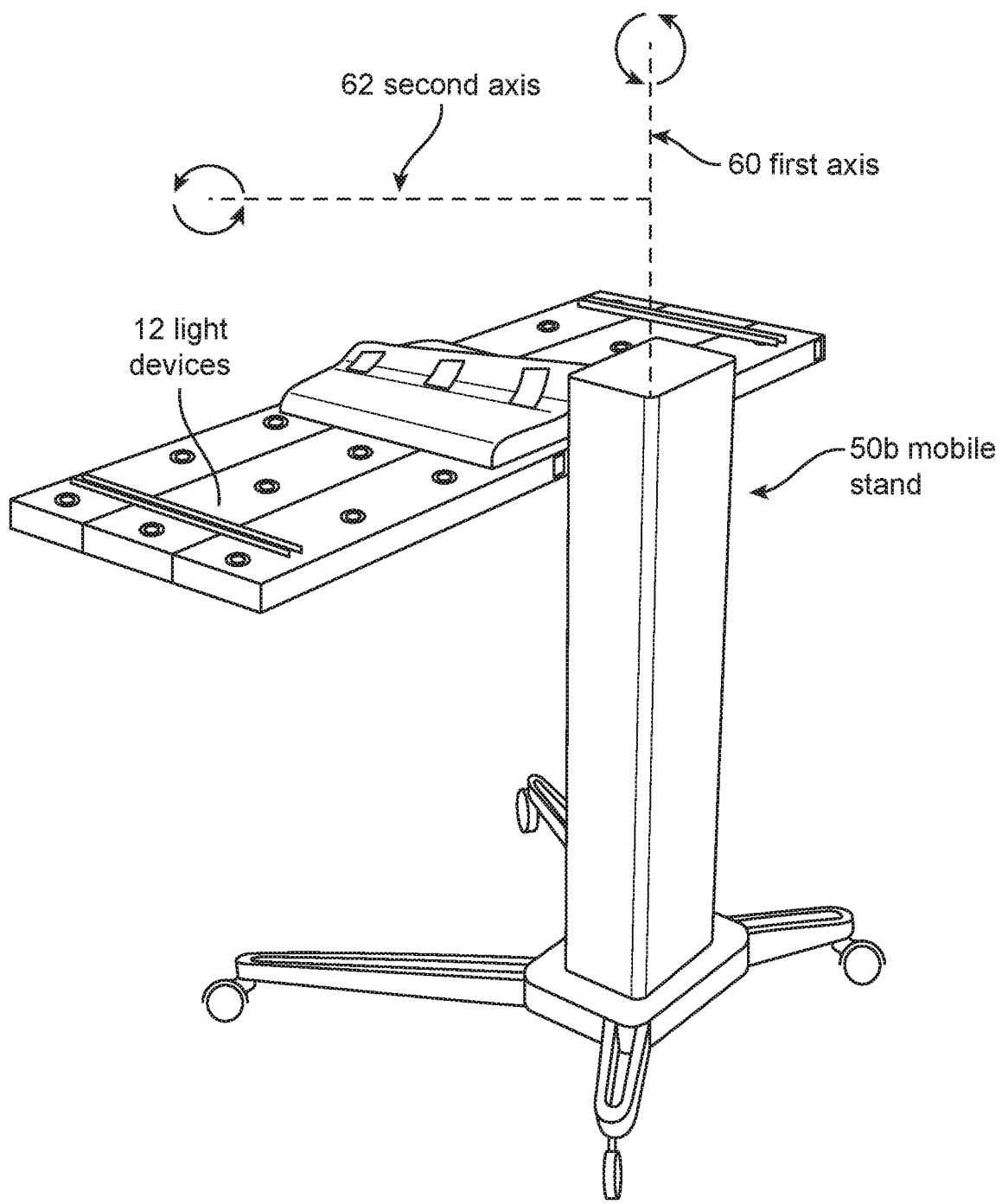
FIG. 17 illustrates a perspective view of a light therapy system mounted to a mobile stand in which a first and second light device have a first form factor, and a third and fourth light device have a second form factor.

FIG. 17 shows yet another embodiment of a mobile stand 50b. In this embodiment, the mobile stand 50b is configured such that the light devices 12 can be rotated on a first axis 60 and/or a second axis 62. Being able to rotate the light devices 12 along two axes 60, 62 may allow the system 10 to be moved into any possible position to accommodate a desired treatment. For example, if a person is lying down on a flat surface, such as a bed, the light devices 12 can be aimed downwards toward the flat surface, and treatment can be applied to a user's entire front or back side.

Figure 16:
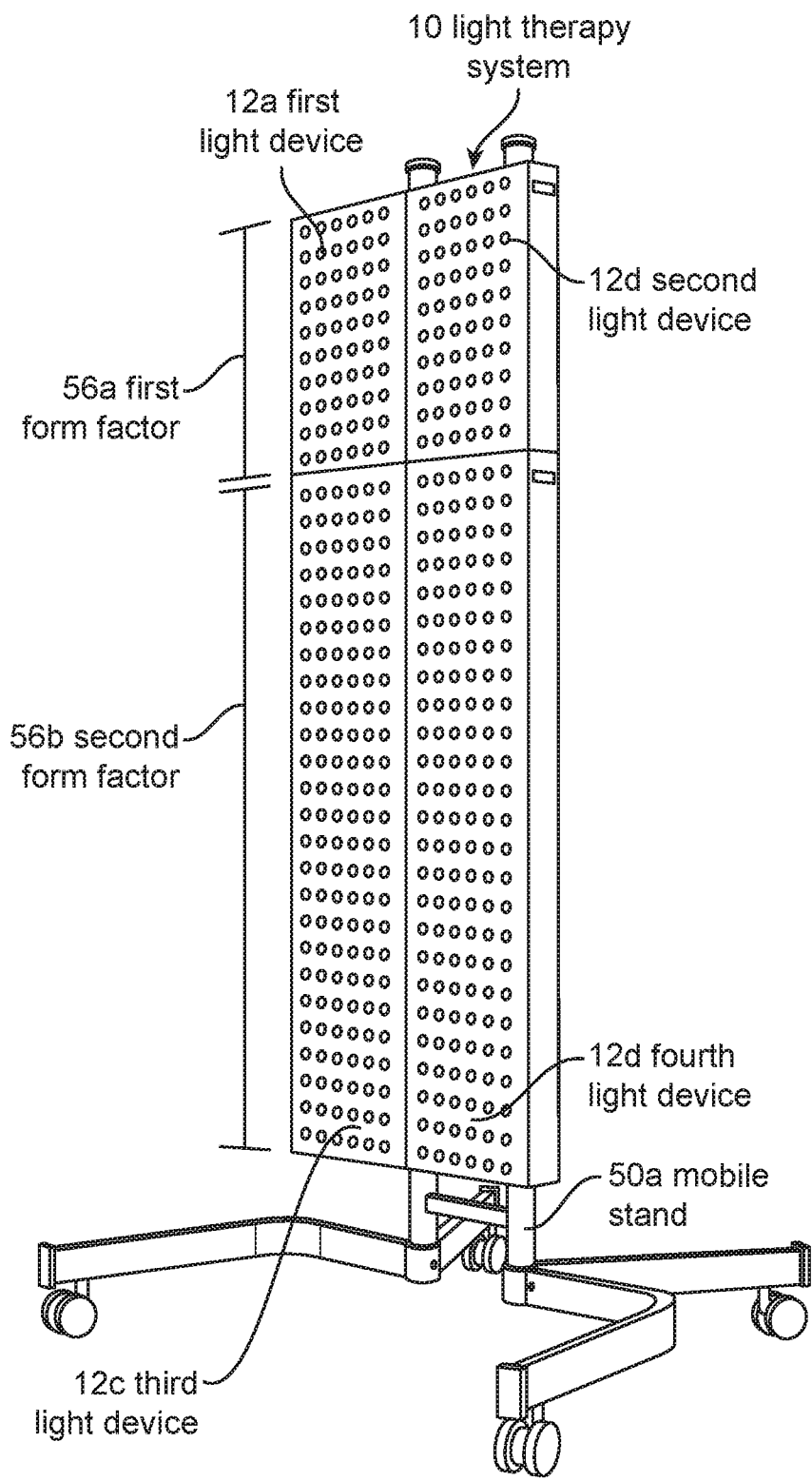
FIG. 16 illustrates a perspective view of one possible embodiment of a light therapy system mounted to a mobile stand that is capable of rotation on two axes.
Figure 19:
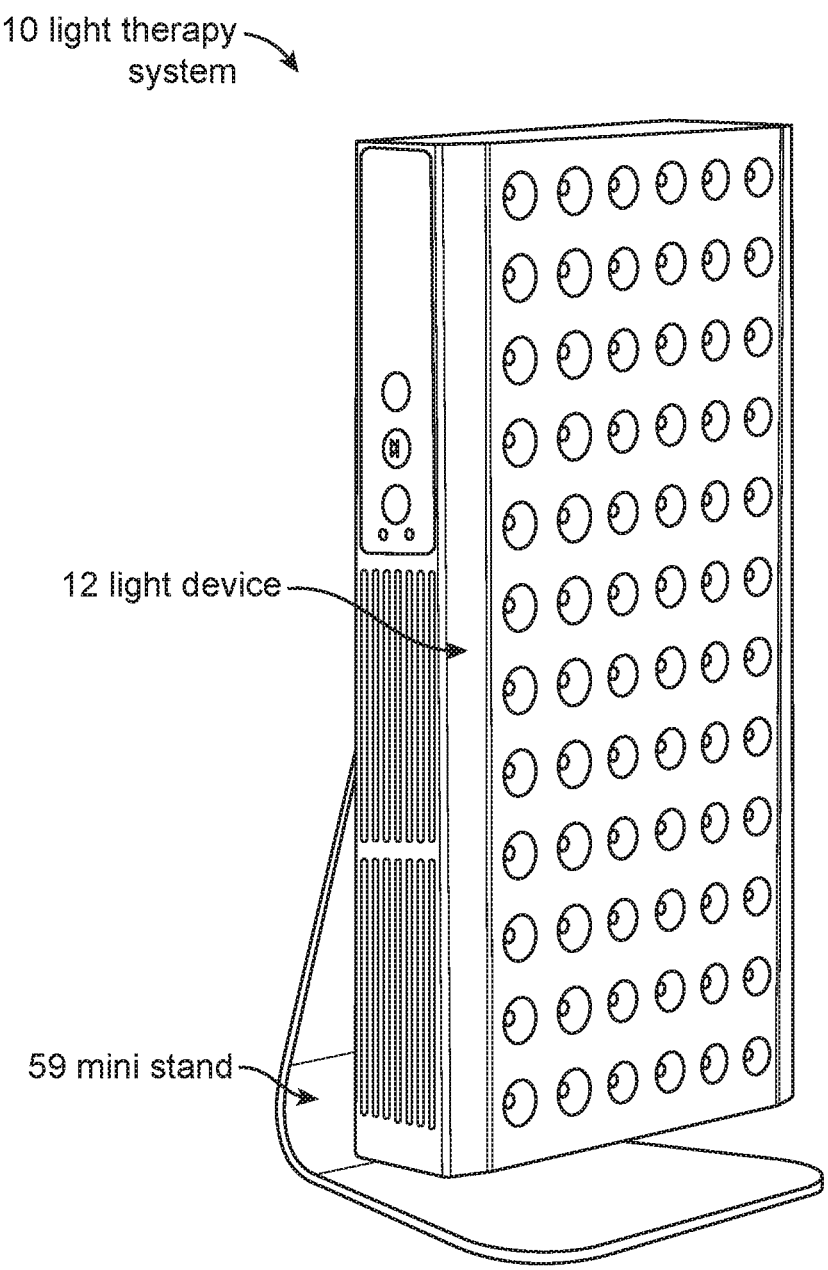
FIG. 19 illustrates a perspective view of a light therapy system that includes a mini stand.

With regards to FIGS. 16 and 19, the light devices 12 may define more than one form factor 56. FIG. 16 shows an embodiment in which the light therapy system 10 is made up of light devices 12 with two different form factors 56a and 56b. The first form factor 56a in FIG. 16 is shorter than the second form factor 56b. Different form factors 56 can be advantageous in situations when a larger treatment area is required than one light device 12 can provide, but there is a lack of space for a second equal size light device 12. Another benefit is that smaller form factors 56a cost less than a larger form factors 56b. In this regard, a user may purchase a smaller light device, such as an entry level device, and then add on to the system 10 once they become familiar and comfortable with the performance of the smaller light device. In some embodiments, the different form factors 56 may be configured to be modular. In this way, any amount of smaller form factor 56a light devices 12 and larger form factor 56b light devices may be mechanically coupled together in either a side-by-side orientation or a top-to-bottom orientation. This allows the light therapy system 10 to be configured into a customizable shape and size for unique treatment areas.

Figure 18A:
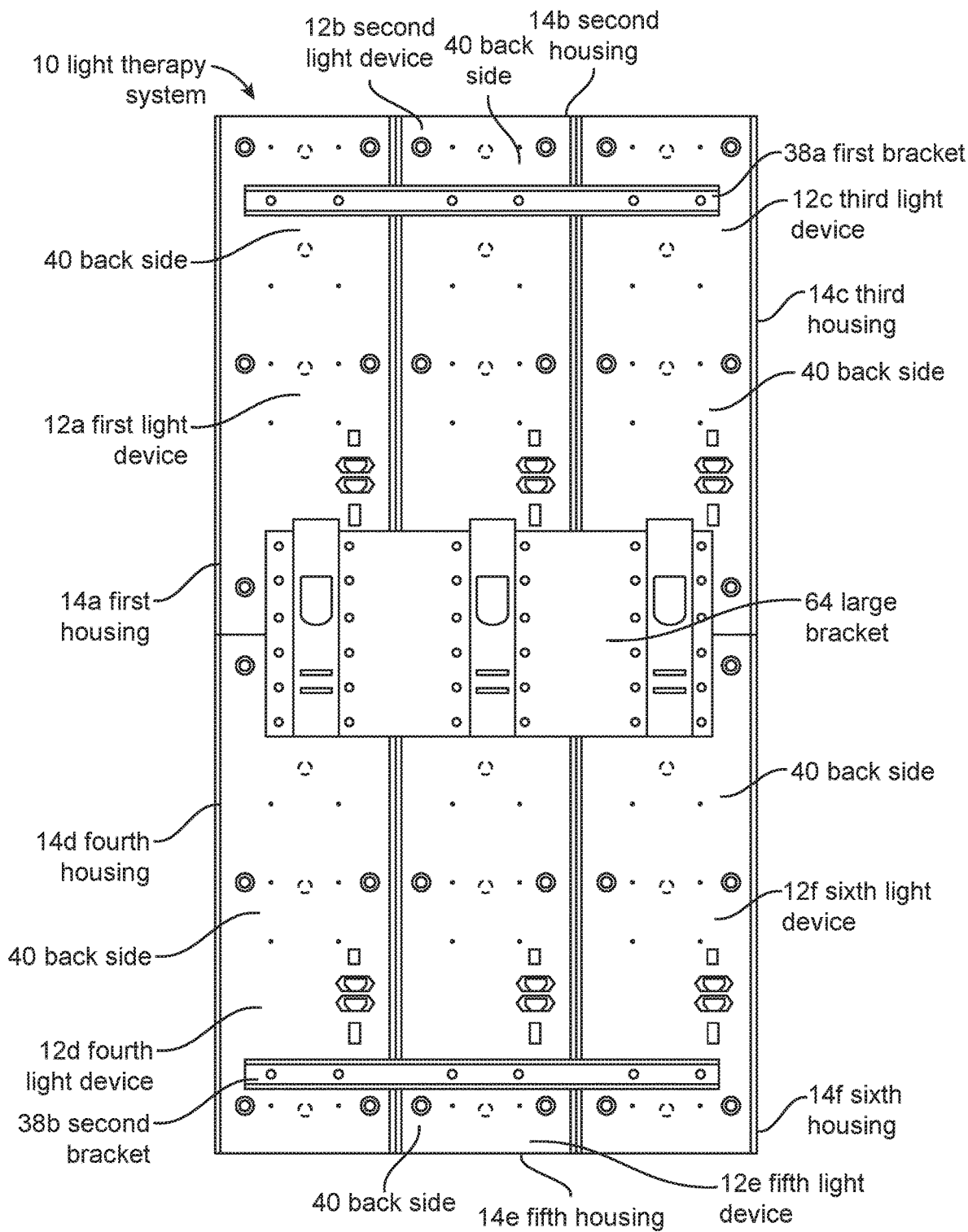
FIG. 18A illustrates a back view of a light therapy system in which first, second, third, fourth, fifth, and sixth light devices are mechanically coupled via a first bracket, a second bracket, and a large bracket.
Figure 18B:
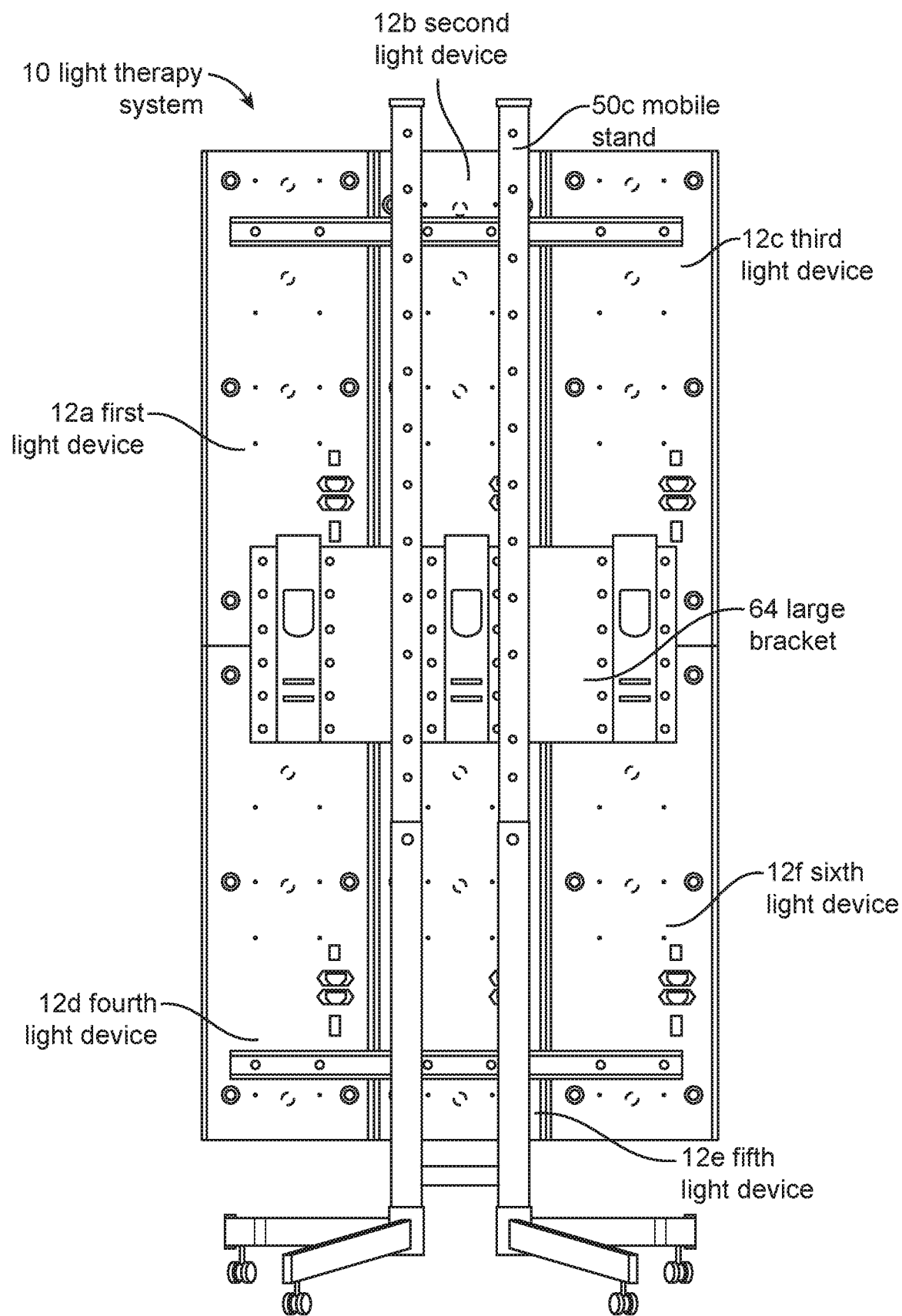
FIG. 18B illustrates a back view of a light therapy system in which first, second, third, fourth, fifth, and sixth light devices are mechanically coupled via a first bracket, a second bracket, and a large bracket that is mechanically coupled with a mobile stand.

An example of a modular embodiment can be seen in FIG. 18A. The illustration shows six light devices 12a, 12b, 12c, 12d, 12e, and 12f mechanically coupled into a two by three grid. Light devices 12a, 12b, and 12c are coupled together via the first bracket 38a, and the light devices 12d, 12e, and 12f are coupled together via the second bracket 38b. As shown, the large bracket 64 located in the middle may mechanically couple all six of the light devices 12 together. FIG. 18B shows an embodiment in which the large bracket 64 also serves as a mount to couple the light system 10 to a mobile stand 50c.

Generally, FIGS. 18A and 18B illustrate the potential for expansion of the system 10. Accordingly, it should be appreciated that any size and shape of brackets 38, 44 may be used to accommodate expansion beyond six light devices 12. In this regard, the system 10 may be configured to have 8, 10, 12, 14, 16, and 24 or more light devices 12 working together as one unified light therapy system 10.

With reference to FIG. 19, the disclosure includes a mini stand 59 that allows the light therapy system and/or one or more light devices (12) to be mounted on a table top, desk, counter, and the like. In this regard, the mini stand 59 may be arranged and configured to couple to a light device 12, such as a smaller light device 12, or plurality of light devices 12 all of which may define smaller form factors sized and configured to sit atop a table top, etc. The mini stand 59 may be able to pivot, raise, and/or lower in any direction with respect to the base of the mini stand 59.

Figure 20:
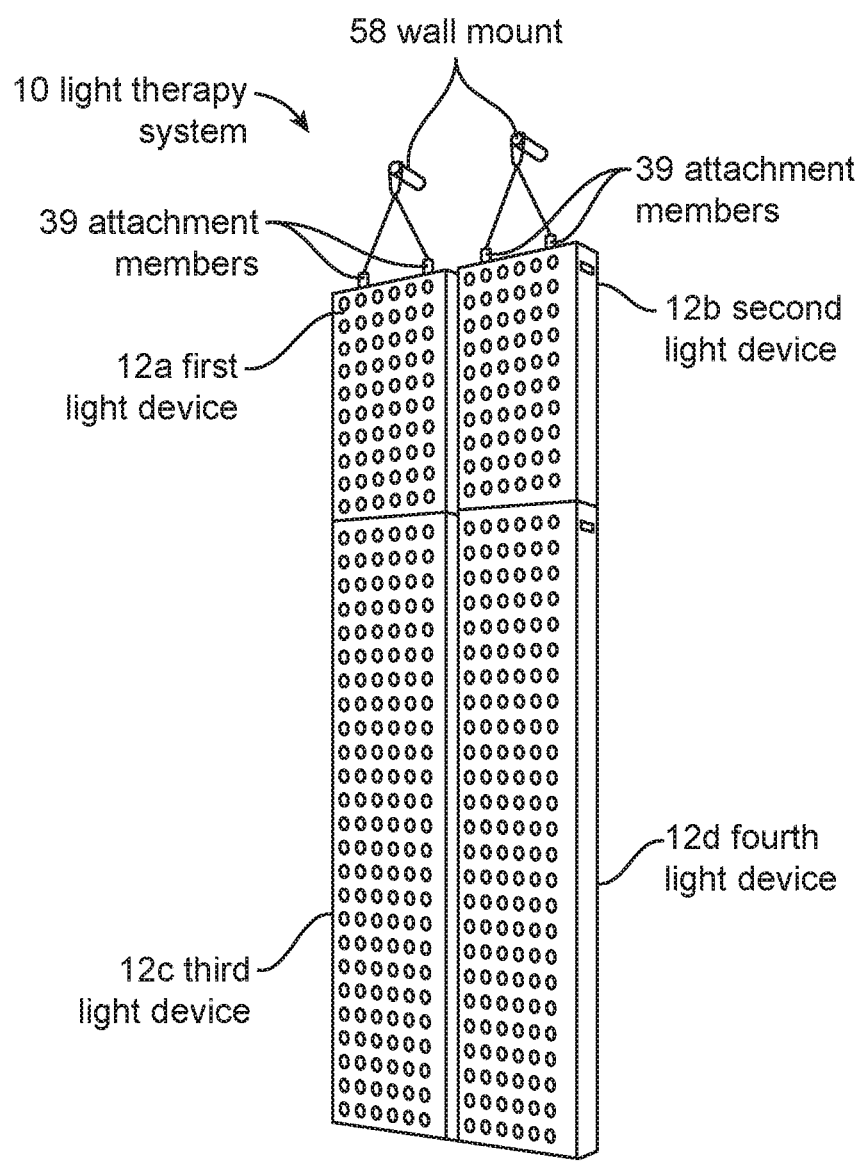
FIG. 20 illustrates a perspective view of a light therapy system that includes a wall mount for attaching the system to a substrate, such as a wall.

As shown in FIG. 20, the system 10 and/or one or more light devices 12 may also be coupled to a wall mount 58, which can be mounted to a substrate, such as a wall. Specifically, the system 10 may include one or more attachment members 39 located at the top of the respective light device(s) 12. A first portion of the wall mount 58 may thereby be coupled to a wall, while a second portion of the wall mount 58 may be coupled to the attachment member(s) 39 to thereby couple the system 10 and/or light device(s) 12 to the substrate or wall. In this regard, the wall mount 58 may allow the system 10 and/or light device(s) 12 to be mounted in an easy to reach location yet physically situated out of the way to thereby reduce space requirements. Similar to any of the embodiments described throughout, the wall mount 58 may be used to mount one light device 12 or two or more light devices 12.

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

Some of the devices, systems, embodiments, and processes use computers. Each of the routines, processes, methods, and algorithms described in the preceding sections may be embodied in, and fully or partially automated by, code modules executed by one or more computers, computer processors, or machines configured to execute computer instructions. The code modules may be stored on any type of non-transitory computer-readable storage medium or tangible computer storage device, such as hard drives, solid state memory, flash memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

The following is claimed:

1. A photobiomodulation therapy system, comprising:
a first light device including a first rigid housing having a first front surface and a first back surface facing opposite the first front surface, a first printed circuit board (PCB) located within the first rigid housing, and a first plurality of light sources electrically coupled to the first PCB and configured to emit light from the first front surface, wherein the first plurality of light sources are at least partially encompassed within the first rigid housing and thereby at least partially protrude through the first rigid housing, and wherein a first portion of the first plurality of light sources emits near infrared light and a second portion of the first plurality of light sources emits red light;
a second light device arranged and configured to be detachably coupled to the first light device, the second light device including a second rigid housing having a second front surface and a second back surface facing opposite the second front surface, a second printed circuit board (PCB) located within the second rigid housing, and a second plurality of light sources electrically coupled to the second PCB and configured to emit light from the second front surface, wherein the second plurality of light sources are at least partially encompassed within the second rigid housing and thereby at least partially protrude through the second rigid housing, and wherein a first portion of the second plurality of light sources emits near infrared light and a second portion of the second plurality of light sources emits red light;
a first bracket arranged and configured to be detachably coupled to the first back surface and the second back surface to thereby detachably couple the first rigid housing to the second rigid housing, wherein the first bracket defines a first bracket width and a first bracket height extending opposite the first bracket width, and wherein at least one of the first bracket width is less than a width of the first rigid housing and a width of the second rigid housing, and the first bracket height is less than a height of the first rigid housing and a height of the second rigid housing;
a first aperture located on a bottom side of the first rigid housing;
a second aperture located on the bottom side of the first rigid housing;
a first attachment member extending from a top surface of the second rigid housing, wherein the first attachment member is arranged and configured to be detachably coupled to the first aperture to thereby couple the first rigid housing to the second rigid housing; and
a second attachment member extending from the top surface of the second rigid housing, wherein the second attachment member is arranged and configured to be detachably coupled to the second aperture to thereby couple the first rigid housing to the second rigid housing.

2. The system of claim 1, further comprising a second bracket arranged and configured to be detachably coupled to the first back surface and the second back surface to thereby detachably couple the first rigid housing to the second rigid housing.

3. The system of claim 2, further comprising:
a third light device including: a third rigid housing having a third front surface and a third back surface facing opposite the third front surface whereby the third rigid housing is arranged and configured to be detachably coupled to at least one of the first light device and the second light device; a third printed circuit board (PCB) located within the third rigid housing; and a third plurality of light sources electrically coupled to the third PCB, wherein the third plurality of light sources are at least partially encompassed within the third rigid housing and thereby at least partially protrude through the third rigid housing, and wherein a first portion of the third plurality of light sources emits near infrared light and a second portion of the third plurality of light sources emits red light;
a fourth light device including: a fourth rigid housing having a fourth front surface and a fourth back surface facing opposite the fourth front surface whereby the fourth rigid housing is arranged and configured to be detachably coupled to at least one of the first light device, the second light device, and the third light device; a fourth printed circuit board (PCB) located within the fourth rigid housing; and a fourth plurality of light sources electrically coupled to the fourth PCB, wherein the fourth plurality of light sources are at least partially encompassed within the fourth rigid housing and thereby at least partially protrude through the fourth rigid housing, and wherein a first portion of the fourth plurality of light sources emits near infrared light and a second portion of the fourth plurality of light sources emits red light;
a third bracket arranged and configured to be detachably coupled to the third back surface and the fourth back surface to thereby detachably couple the third rigid housing to the fourth rigid housing; and
a fourth bracket arranged and configured to be detachably coupled to the third back surface and the fourth back surface to thereby detachably couple the third rigid housing to the fourth rigid housing.

4. The system of claim 3, further comprising
a third aperture and a fourth aperture both located on a bottom surface of the second rigid housing.

5. The system of claim 1, wherein the first bracket width is less than a width of the first rigid housing and a width of the second rigid housing, and the first bracket height is less than a height of the first rigid housing and a height of the second rigid housing.

6. The system of claim 2, wherein the second bracket defines a second bracket width and a second bracket height extending opposite the second bracket width, and
wherein at least one of the second bracket width is less than a width of the first rigid housing and a width of the second rigid housing, and the second bracket height is less than a height of the first rigid housing and a height of the second rigid housing.

7. The system of claim 6, wherein the second bracket width is less than the width of the first rigid housing and the width of the second rigid housing, and the second bracket height is less than the height of the first rigid housing and the height of the second rigid housing.

8. The system of claim 1, further comprising:
a third attachment member extending from a top surface of the first rigid housing; and
a fourth attachment member extending from the top surface of the first rigid housing.

9. The system of claim 3, wherein the third bracket defines a third bracket width and a third bracket height extending opposite the third bracket width,
wherein at least one of the third bracket width is less than a width of the third rigid housing and a width of the fourth rigid housing, and the third bracket height is less than a height of the third rigid housing and a height of the fourth rigid housing.

10. The system of claim 9, wherein the third bracket width is less than the width of the third rigid housing and the width of the fourth rigid housing, and the third bracket height is less than the height of the third rigid housing and the height of the fourth rigid housing.

11. The system of claim 3, wherein the fourth bracket defines a fourth bracket width and a fourth bracket height extending opposite the fourth bracket width, and wherein at least one of the fourth bracket width is less than a width of the third rigid housing and a width of the fourth rigid housing, and the fourth bracket height is less than a height of the third rigid housing and a height of the fourth rigid housing.

12. The system of claim 11, wherein the fourth bracket width is less than the width of the third rigid housing and the width of the fourth rigid housing, and the fourth bracket height is less than the height of the third rigid housing and the height of the fourth rigid housing.

13. The system of claim 3, wherein the second bracket is arranged and configured to be detachably coupled to the first back surface, the second back surface, the third back surface, and the fourth back surface to thereby detachably couple the first rigid housing, the second rigid housing, the third rigid housing, and the fourth rigid housing together.

14. The system of claim 13, further comprising a mobile stand arranged and configured to be detachably coupled to the second bracket.

15. The system of claim 4, further comprising a first pair of attachment members extending from a top surface of the third rigid housing, wherein the first pair of attachment members is arranged and configured to be detachably coupled to the first aperture and the second aperture.

16. The system of claim 15, further comprising a second pair of attachment members extending from the top surface of the fourth rigid housing, wherein the second pair of attachment members is arranged and configured to be detachably coupled to the third aperture and the fourth aperture.

17. The system of claim 4, further comprising a fifth attachment member extending from a top surface of the third rigid housing, wherein the fifth attachment member is arranged and configured to be detachably coupled to the first aperture.

18. The system of claim 17, further comprising a sixth attachment member extending from the top surface of the third rigid housing, wherein the sixth attachment member is arranged and configured to be detachably coupled to the second aperture.

19. The system of claim 18, further comprising a seventh attachment member extending from a top surface of the fourth rigid housing, wherein the seventh attachment member is arranged and configured to be detachably coupled to the third aperture.

20. The system of claim 19, further comprising an eighth attachment member extending from the top surface of the fourth rigid housing, wherein the eighth attachment member is arranged and configured to be detachably coupled to the fourth aperture.

* * * * *